United States Patent [19]

Arvesen

[11] 4,236,211
[45] Nov. 25, 1980

[54] METHOD AND APPARATUS FOR DETERMINING THE MINIMUM CONCENTRATION OF ANTIBIOTIC NECESSARY TO AT LEAST INHIBIT MICROORGANISM GROWTH

[75] Inventor: James N. Arvesen, Princeton, N.J.

[73] Assignee: Pfizer Inc., New York, N.Y.

[21] Appl. No.: 942,683

[22] Filed: Sep. 15, 1978

[51] Int. Cl.³ .................. G06F 15/20; C12Q 1/18; G01N 21/00
[52] U.S. Cl. .................. 364/413; 356/246; 356/440; 422/68; 364/497; 435/32; 435/291; 435/808
[58] Field of Search .............. 364/413, 497, 498, 499; 23/230 B; 422/67, 68, 63; 195/127, 103.5 R, 103.5 K; 356/440, 246, 435; 435/3, 32, 33, 291, 300, 808, 809

[56] References Cited

U.S. PATENT DOCUMENTS

| D. 230,587 | 3/1974 | Praglin et al. | D16/2 C |
|---|---|---|---|
| D. 240,052 | 5/1976 | Varga et al. | D32/2 C |
| 3,832,532 | 8/1974 | Praglin et al. | 195/103.5 R X |
| 3,837,745 | 9/1974 | Acker et al. | 195/127 X |
| 3,837,746 | 9/1974 | Acker et al. | 195/127 X |
| 3,895,661 | 7/1975 | Praglin et al. | 195/127 X |
| 3,899,011 | 8/1975 | Curtiss | 195/127 X |
| 3,983,006 | 9/1976 | Acker et al. | 195/127 |

OTHER PUBLICATIONS

Ericsson et al., "Antibiotic Sensitivity Testing Report of an International Collaborative Study", Acta Pathologica et Microbiologica Scandinavica, Section B, 1971, Supplement No. 217,19.
Bauer et al., "Antibiotic Susceptibility Testing by a Standardized Single Disk Method", The American Journal of Clinical Pathology, 1966, vol. 45, No. 4.
Lennette et al., Manual of Clinical Microbiology, 2nd Edition, published by American Soc. for Microbiology, 1974.
Balows, "Current Techniques for Antibiotic Susceptibility Testing", publ. by Charles C. Thomas (1974).
McDowan, Jr. et al., "Rapid Semiquantitative Testing of Antibiotic Susceptibility: Use of a Multicell Disk Elution System", Antimicrob. Agents Chemother., May 1975, pp. 543-548, American Soc. for Microbiology.

Primary Examiner—Joseph F. Ruggiero
Attorney, Agent, or Firm—Cushman, Darby & Cushman

[57] ABSTRACT

A fixed functional relationship in either tabular or equation form is established between the growth of various microorganisms in the presence of a few (e.g., one or two) predetermined concentrations of a predetermined antibiotic and the minimum concentration of such antibiotic necessary to at least inhibit the activity of such samples. The relationships are established for each desired combination of antibiotic and general class of microorganisms and the degree of growth is measured at a predetermined time or level of growth, preferably before saturation occurs at "growth" or "no growth" extremes. The minimum concentrations used in deriving these fixed relationships are determined by standard accepted quantitative techniques. Thereafter, the minimum concentration of the predetermined antibiotic necessary to at least inhibit the activity of any given pathogenic microorganism taken from the same predetermined general class of organisms may be rapidly and accurately determined by (1) measuring the growth of such sampled pathogenic organism after the same predetermined time in the presence of the same few (e.g., one or two) predetermined concentrations of the antibiotic and (2) using the resulting measurements together with the previously established fixed functional relationship to identify the required minimum concentration for that particular combination of microorganism and antibiotic. Apparatus for semiautomatically and for automatically carrying out this method are also disclosed.

37 Claims, 39 Drawing Figures

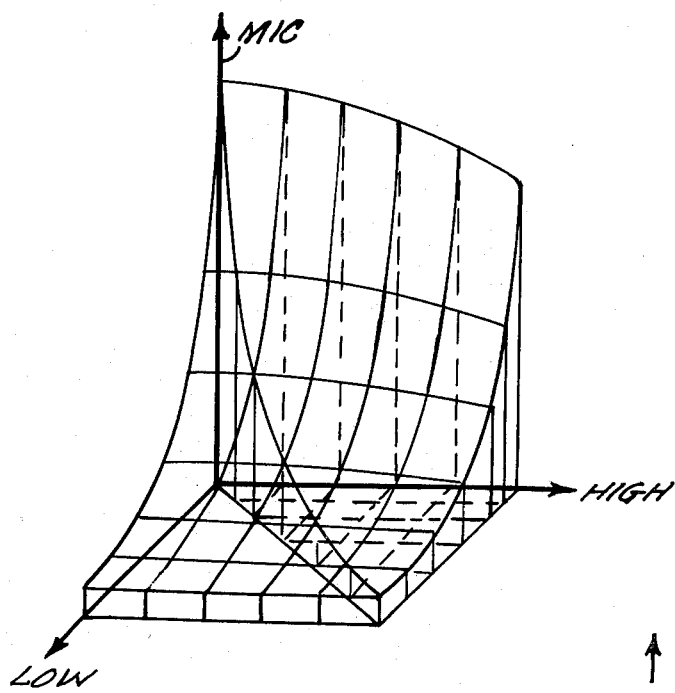
FIG. 4a
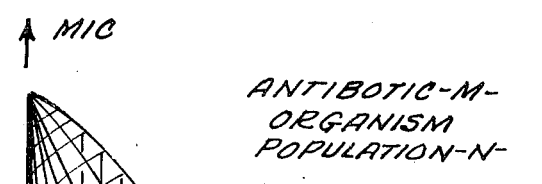
FIG. 4b
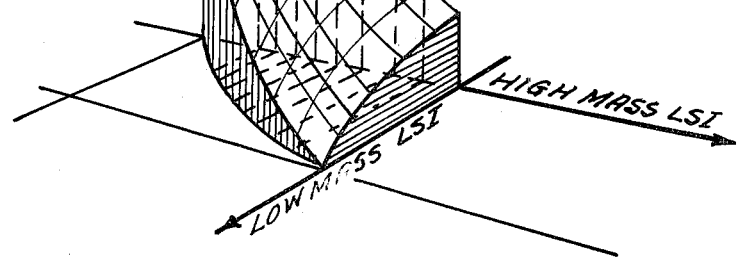
FIG. 4c
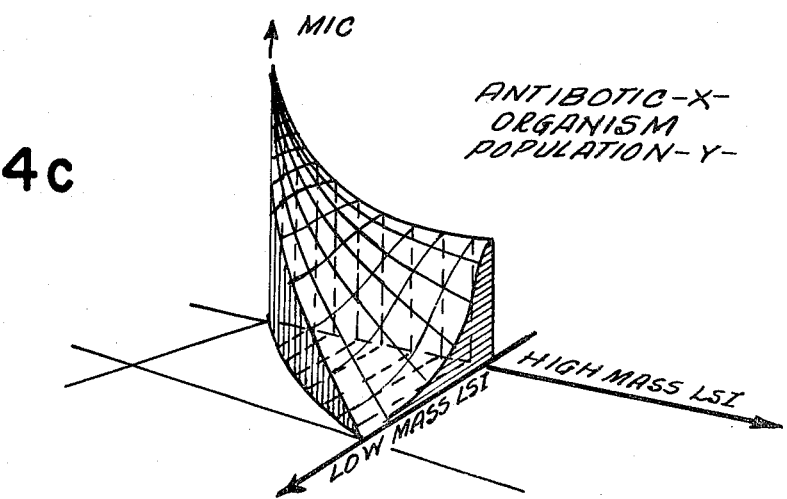

REGRESSION EQUATIONS* USED TO DETERMINE AUTOBAC MIC VALUES FOR
GRAM POSITIVE ORGANISMS

| | STAPHYLOCOCCI | | ENTEROCOCCI |
|---|---|---|---|
| | $LSI_{48} \leq .65$ | $LSI_{48} > .65$ | |
| AMPICILLIN | | | $= 35.08[-\exp(.05\ LSI_3) + 1.32313\ \exp(-.23\ LSI_{48})]$ |
| CEPHALOTHIN | $= 6.2911\ \exp(-.14\ LSI_3)$ $+ 1.70893\ \exp(-4.24\ LSI_{48})$ | $= 7.13971\ \exp(-.92\ LSI_3)$ $- 1.1004\ \exp(.95\ LSI_{48})$ | $= 832.8[1.0135\ \exp(-.00369\ LSI_3) - \exp(.00725\ LSI_{48})]$ |
| CHLORAMPHENICOL | $= 6.894 - 7.873(LSI_{12}) + 3.216(LSI_{12})^2$ | | $= 11.67[1.67218\ \exp(-.27\ LSI_{12}) - \exp(.10\ LSI_{48})]$ |
| CLINDAMYCIN | $= 89.31[1.04479\ \exp(-.00452\ LSI_{1.5}) - \exp(.05\ LSI_6)]$ | | |
| GENTAMICIN | $= 4.03909\ \exp(-2.278\ LSI_3) - .0390864\ \exp(2.360\ LSI_{12})$ | | |
| METHICILLIN | $= 4.918 - 2.178(LSI_3) - 2.337(LSI_{12})^2$ | | |
| PENICILLIN G | $= 11.33[-\exp(.385\ LSI_{.188}) + 1.51151\ \exp(-.343\ LSI_{48})]$ | | $= 11.9148\ \exp(-.5\ LSI_{12}) - 3.17015\ \exp(.5\ LSI_{48})$ |
| TETRACYCLINE | $= 8.60602\ \exp(-1.295\ LSI_3) - 2.60604\ \exp(.092\ LSI_{12})$ | | $= 8.01149\ \exp(-1.06\ LSI_3) - 2.5115\ \exp(.1\ LSI_{12})$ |

* The above equations yield MIC values (in mcg/ml or units/ml for penicillin G) expressed as $\log_2$ MIC.

FIG. 7

REGRESSION EQUATIONS* USED TO DETERMINE AUTOBAC MIC VALUES FOR GRAM NEGATIVE ORGANISMS

| | ENTEROBACTERIACEAE | PSEUDOMONAS and ACINETOBACTER SP. |
|---|---|---|
| AMPICILLIN | $= 7.118 - 4.627(LSI_3) - 2.115(LSI_{48})^2$ | $= 7.059 - 2.639(LSI_{48})^2 - 5.317(LSI_3)^3$ |
| CARBENICILLIN | $= 9.402 - 9.705(LSI_{12}) - 2.228(LSI_{192}) + 4.661(LSI_{12})^2$ | $LSI_{192} \leq .85$: $= 9.665 - 4.961(LSI_{192}) - 3.816(LSI_{12})^2$ \| $LSI_{192} > .85$: $= 5.963 - 3.029(LSI_{12})$ |
| CEPHALOTHIN | $= 6.908 - 3.970 LSI_3 + 3.064 LSI_{48} + 1.766(LSI_3)^2 - 6.622(LSI_{48})^2$ | $= 9.97899 \exp(-.554 LSI_3) - 1.97898 \exp(.635 LSI_{48})$ |
| CHLORAMPHENICOL | $= 6.973 - 2.035(LSI_{48}) - 2.341(LSI_{12})^2$ | $= 7.143 - 2.870(LSI_{12})^2 - 1.161(LSI_{48})^2$ |
| GENTAMICIN | $= 4.067 - 4.756(LSI_3) - 1.338(LSI_{12}) + 2.108(LSI_3)^2$ | $= 5.052 - 2.689(LSI_3)^2 - 1.636(LSI_{12})$ |
| KANAMYCIN | $= 6.295 - 2.747(LSI_6) + 1.361(LSI_6)^2 - 6.766(LSI_{24}) + 2.993(LSI_{24})^2$ | $= 11.4402 \exp(-.4 LSI_6) - 4.94023 \exp(.3 LSI_{24})$ |
| PENICILLIN G | $= 6.972 - 2.252(LSI_{48}) - 3.214(LSI_{12})^2$ | |
| TETRACYCLINE | $= 7.34428 \exp(-.79 LSI_3) - 1.84429 \exp(.0975 LSI_{12})$ | $= 5.126 - 2.902(LSI_3)^2 - 1.629(LSI_{12})^2$ |

* The above equations yield MIC values (in mcg/ml or units/ml for penicillin G) expressed as $\log_2$ MIC.

FIG. 8

AUTOBAC MIC PERFORMANCE LIMITS

| Antibiotic | Autobac MIC Values (micrograms per milliliter)[1] | | | |
|---|---|---|---|---|
| | Staphylococci | Enterococci | Enterobacteriaceae | Pseudomonas and Acinetobacter SP. |
| Ampicillin | NR[2] | ≤1 -- >64 | ≤1.5 -- >64 | ≤1 -- >64 |
| Carbenicillin | NR | NR | ≤4 -- >256 | ≤12 -- >256 |
| Cephalothin | ≤1 -- >64 | ≤4 -- >64 | ≤2 -- >64 | ≤4 -- >64 |
| Chloramphenicol | ≤4 -- >64 | ≤4 -- >64 | ≤6 -- >64 | ≤8 -- >64 |
| Clindamycin | ≤.5 -- >8 | NR | NR | NR |
| Gentamicin | ≤1 -- ≥16 | NR | ≤1 -- ≥16 | ≤2 -- >16 |
| Kanamycin | NR | NR | ≤2 -- >32 | ≤2 -- >32 |
| Methicillin | ≤1.5 -->16 | NR | NR | NR |
| Penicillin G | ≤0.063 -- ≥64 | ≤4 -- >64 | ≤3 -- >64 | NR |
| Tetracycline | ≤1 -- >16 | ≤1 -- >16 | ≤2 -- >16 | ≤1.5 -- >16 |

1 Penicillin - units/ml

2 Not recommended

FIG. 9

PERCENT AGREEMENT (WITHIN ± ONE TWO-FOLD DILUTION)
BETWEEN THE MIC VALUES OBTAINED WITH THE AUTOBAC METHOD
(USING REGRESSION ANALYSIS) AND THE REFERENCE METHOD - PHASE I

| | GAVAN | | | SCHOENKNECHT | | | THORNSBERRY | | | WASHINGTON | | | AVERAGE | | |
|---|---|---|---|---|---|---|---|---|---|---|---|---|---|---|---|
| | GP+1 | GP-1 | GP-2 | GP+1 | GP-1 | GP-2 | GP+1 | GP-1 | GP-2 | GP+1 | GP-1 | GP-2 | GP+1 | GP-1 | GP-2 |
| AMPICILLIN | - | 100% 92.0% | 96.7% | - | 100% 94.3% | 96.7% | - | 100% 89.1% | 91.7% | - | 95.0% 86.3% | 95.0% | - | 98.8% 90.4% | 95.0% |
| | (n=255) 93.7% | | | (n=255) 95.3% | | | (n=255) 90.6% | | | (n=255) 89.0% | | | (n=1020) 92.2% | | |
| CARBENICILLIN | - | 85.4% 86.7% | | - | 98.3% 85.0% | | - | 94.3% 83.3% | | - | 96.0% 90.0% | | - | 95.9% 86.2% | |
| | (n=235) 93.2% | | | (n=235) 94.9% | | | (n=235) 91.5% | | | (n=235) 94.5% | | | (n=940) 93.5% | | |
| CEPHALOTHIN | 100% | 95.0% 94.3% | 100% | 100% | 100% 93.1% | 98.3% | 96.7% | 100% 95.4% | 98.3% | 93.3% | 85.0% 93.1% | 100% | 97.5% | 87.5% 94.0% | 99.2% |
| | (n=315) 94.6% | | | (n=315) 95.9% | | | (n=315) 96.5% | | | (n=315) 94.0% | | | (n=1260) 95.2% | | |
| CHLORAMPHENICOL | 100% | 100% 98.3% | 95.0% | 100% | 100% 97.7% | 95.0% | 100% | 100% 98.3% | 98.3% | 98.3% | 100% 98.3% | 98.3% | 99.6% | 97.5% 98.1% | 96.7% |
| | (n=315) 98.1% | | | (n=315) 97.1% | | | (n=315) 98.7% | | | (n=315) 98.4% | | | (n=1260) 98.1% | | |
| CLINDAMYCIN | 100% | - | - | 98.3% | - | - | 90.0% | - | - | 100% | - | - | 97.1% | - | - |
| | (n=60) 100% | | | (n=60) 98.3% | | | (n=60) 90.0% | | | (n=60) 100% | | | (n=240) 97.1% | | |
| GENTAMICIN | 100% | 98.9% 100% | | 95.0% | 99.4% 95.0% | | 96.7% | 97.1% 93.1% | | 83.1% | 98.9% 93.3% | | 93.8% | 90.6% 95.4% | |
| | (n=295) 99.3% | | | (n=295) 97.6% | | | (n=295) 96.3% | | | (n=295) 94.6% | | | (n=1180) 96.9% | | |
| KANAMYCIN | - | 96.6% 98.3% | | - | 97.1% 98.3% | | - | 94.9% 98.3% | | - | 99.4% 98.3% | | - | 97.0% 98.3% | |
| | (n=235) 97.0% | | | (n=235) 97.4% | | | (n=235) 95.7% | | | (n=235) 99.1% | | | (n=940) 97.3% | | |
| METHICILLIN | 93.3% | - | - | 96.7% | - | - | 93.3% | - | - | 85.0% | - | - | 92.1% | - | - |
| | (n=60) 93.3% | | | (n=60) 96.7% | | | (n=60) 93.3% | | | (n=60) 85.0% | | | (n=240) 92.1% | | |
| PENICILLIN G | 85.0% | 95.0% 97.1% | | 83.1% | 100% 93.7% | | 80.0% | 100% 99.4% | | 86.7% | 75.0% 98.9% | | 83.8% | 92.5% 97.3% | |
| | (n=255) 94.1% | | | (n=255) 91.8% | | | (n=255) 94.9% | | | (n=255) 94.1% | | | (n=1020) 93.7% | | |
| TETRACYCLINE | 96.7% | 100% 89.7% | 98.3% | 90.0% | 95.0% 89.7% | 95.0% | 96.7% | 100% 97.1% | 95.0% | 96.7% | 100% 98.3% | 100% | 95.0% | 98.8% 93.7% | 97.1% |
| | (n=315) 93.3% | | | (n=315) 91.1% | | | (n=315) 96.8% | | | (n=315) 98.4% | | | (n=1260) 94.9% | | |
| AVERAGE | 96.4% | 92.0% 95.3% | 96.4% | 94.8% | 97.0% 95.4% | 94.8% | 93.1% | 100% 95.7% | 94.0% | 91.9% | 91.0% 96.1% | 96.4% | 94.1% | 95.0% 95.6% | 95.4% |
| | (n=2340) 95.5% | | | (n=2340) 95.2% | | | (n=2340) 95.2% | | | (n=2340) 95.2% | | | (n=9360) 95.3% | | |

[1] GP+1 = 60 staphylococci; GP+2 = 20 enterococci; GP-1 = 175 enterobacteriaceae; GP-2 = 60 non-fermenters
[2] (n = total number of strains tested); [3] ±1 four-fold dilution for Penicillin and GP + 1.

TABLE OF AUTOBAC I-MIC VALUES

FOR

AMPICILLIN VS. ENTEROCOCCI

| AUTOBAC I LSI FOR 48 MCG DISK (AM/e3) | | | | | | | | | | | AUTOBAC I LSI FOR 3 MCG DISK (AM/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >64 | >64 | >64 | >64 | >64 | 64 | 48 | 24 | 12 | 6 | 3 | 0.0 |
| >64 | >64 | >64 | >64 | >64 | 64 | 32 | 16 | 12 | 6 | 3 | 0.1 |
| >64 | >64 | >64 | >64 | >64 | 64 | 32 | 16 | 8 | 6 | 3 | 0.2 |
| | >64 | >64 | >64 | >64 | 48 | 32 | 16 | 8 | 4 | 2 | 0.3 |
| | | >64 | >64 | >64 | 48 | 24 | 12 | 8 | 4 | 2 | 0.4 |
| | | | >64 | >64 | 48 | 24 | 12 | 6 | 3 | 2 | 0.5 |
| | | | | 64 | 32 | 16 | 12 | 6 | 3 | 1.5 | 0.6 |
| REPEAT TESTING SHOULD BE PERFORMED FOR ORGANISMS WITH PAIRS OF LSI VALUES IN THIS REGION | | | | | 32 | 16 | 8 | 4 | 3 | 1.5 | 0.7 |
| | | | | | | 16 | 8 | 4 | 2 | 1.5 | 0.8 |
| | | | | | | | 8 | 4 | 2 | ≤1 | 0.9 |
| | | | | | | | | 3 | 2 | ≤1 | 1.0 |

MIC = antilog$_2$ {35.08[-exp(.05 LSI$_3$)+1.32313 exp(-.23 LSI$_{48}$)]}

FIG. 11

FIG. 12
TABLE OF AUTOBAC 1 MIC VALUES
FOR
AMPICILLIN VS. ENTEROBACTERIACEAE

| AUTOBAC 1 LSI FOR 48 MCG DISK (AM/e3) | | | | | | | | | | | AUTOBAC 1 LSI FOR 3 MCG DISK (AM/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >64 | >64 | >64 | >64 | >64 | >64 | >64 | 64 | 48 | 48 | 32 | 0.0 |
| >64 | >64 | >64 | >64 | >64 | 64 | 64 | 48 | 48 | 32 | 24 | 0.1 |
| 64 | 64 | 64 | 64 | 64 | 48 | 48 | 32 | 32 | 24 | 16 | 0.2 |
|  | 48 | 48 | 48 | 48 | 32 | 32 | 24 | 24 | 16 | 12 | 0.3 |
|  |  | 32 | 32 | 32 | 24 | 24 | 16 | 16 | 12 | 8 | 0.4 |
|  |  |  | 24 | 24 | 16 | 16 | 12 | 12 | 8 | 6 | 0.5 |
|  |  |  |  | 16 | 16 | 12 | 12 | 8 | 6 | 4 | 0.6 |
|  |  |  |  |  | 12 | 8 | 8 | 6 | 4 | 3 | 0.7 |
|  |  |  |  |  |  | 6 | 6 | 4 | 3 | 3 | 0.8 |
|  |  |  |  |  |  |  | 4 | 3 | 2 | 2 | 0.9 |
|  |  |  |  |  |  |  |  | 2 | ≤1.5 | ≤1.5 | 1.0 |

REPEAT TESTING SHOULD BE PERFORMED FOR ORGANISMS WITH PAIRS OF LSI VALUES IN THIS REGION $$MIC = antilog_2\{7.118 - 4.627(LSI_3) - 2.115(LSI_{48})^2\}$$

TABLE OF AUTOBAC 1 MIC VALUES

FOR

AMPICILLIN VS. PSEUDOMONAS AND ACINETOBACTER SP.

| AUTOBAC 1 LSI FOR 48 MCG DISK (AM/e3) | | | | | | | | | | | |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >64 | >64 | >64 | >64 | >64 | >64 | 64 | 48 | 48 | 32 | 24 | 0.0 |
| >64 | >64 | >64 | >64 | >64 | >64 | 64 | 48 | 48 | 32 | 24 | 0.1 |
| >64 | >64 | >64 | >64 | >64 | >64 | 64 | 48 | 48 | 32 | 24 | 0.2 |
| | >64 | >64 | >64 | >64 | 64 | 64 | 48 | 32 | 24 | 16 | 0.3 |
| | | >64 | >64 | 64 | 64 | 48 | 48 | 32 | 24 | 16 | 0.4 |
| | | | 64 | 64 | 48 | 48 | 32 | 24 | 16 | 12 | 0.5 |
| | | | | 48 | 32 | 32 | 24 | 16 | 12 | 8 | 0.6 |
| REPEAT TESTING SHOULD BE PERFORMED FOR ORGANISMS WITH PAIRS OF LSI VALUES IN THIS REGION | | | | | 24 | 16 | 16 | 12 | 8 | 6 | 0.7 |
| | | | | | | 12 | 8 | 6 | 4 | 3 | 0.8 |
| | | | | | | | 4 | 3 | 2 | 1.5 | 0.9 |
| | | | | | | | | ≤1 | ≤1 | ≤1 | 1.0 |

(AUTOBAC 1 LSI FOR 3 MCG DISK (AM/e1))

$$\text{MIC} = \text{antilog}_2 \{7.059 - 2.639(\text{LSI}_{48})^2 - 5.317(\text{LSI}_3)^3\}$$

TABLE OF AUTOBAC 1 MIC VALUES

FOR

CARBENICILLIN VS. ENTEROBACTERIACEAE

| AUTOBAC 1 LSI FOR 192 MCG DISK (CB/e3) | | | | | | | | | | | |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >256 | >256 | >256 | >256 | 256 | 256 | 256 | 256 | 192 | 192 | 128 | 0.0 |
| >256 | 256 | 256 | 256 | 192 | 192 | 128 | 128 | 96 | 96 | 64 | 0.1 |
| 192 | 192 | 128 | 128 | 96 | 96 | 96 | 64 | 64 | 48 | 48 | 0.2 |
| | 96 | 96 | 64 | 64 | 48 | 48 | 48 | 32 | 32 | 24 | 0.3 |
| | | 64 | 48 | 48 | 32 | 32 | 24 | 24 | 16 | 16 | 0.4 |
| | | | 32 | 32 | 24 | 24 | 16 | 16 | 12 | 12 | 0.5 |
| | | | | 24 | 16 | 16 | 12 | 12 | 8 | 8 | 0.6 |
| REPEAT TESTING SHOULD BE PERFORMED FOR ORGANISMS WITH PAIRS OF LSI VALUES IN THIS REGION | | | | | 12 | 12 | 12 | 8 | 8 | 6 | 0.7 |
| | | | | | | 8 | 8 | 8 | 6 | 6 | 0.8 |
| | | | | | | | 8 | 6 | 6 | ≤4 | 0.9 |
| | | | | | | | | 6 | 6 | ≤4 | 1.0 |

AUTOBAC 1 LSI FOR 12 MCG DISK (CB/e1)

MIC = antilog$_2$ {9.402 − 9.705(LSI$_{12}$) − 2.228(LSI$_{192}$) + 4.661(LSI$_{12}$)$^2$}

TABLE OF AUTOBAC 1 MIC VALUES

FOR

CEPHALOTHIN VS. PSEUDOMONAS AND ACINETOBACTER SP.

| AUTOBAC 1 LSI FOR 48 MCG DISK (CL/e3) | | | | | | | | | | | AUTOBAC 1 LSI FOR 3 MCG DISK (CL/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >64 | >64 | >64 | >64 | >64 | >64 | >64 | >64 | >64 | >64 | 64 | 0.0 |
| >64 | >64 | >64 | >64 | >64 | >64 | >64 | >64 | 64 | 64 | 48 | 0.1 |
| >64 | >64 | >64 | >64 | >64 | 64 | 64 | 64 | 48 | 48 | 32 | 0.2 |
| | >64 | 64 | 64 | 64 | 48 | 48 | 48 | 32 | 32 | 24 | 0.3 |
| | | 48 | 48 | 48 | 32 | 32 | 32 | 24 | 24 | 16 | 0.4 |
| | | | 32 | 32 | 32 | 24 | 24 | 16 | 16 | 16 | 0.5 |
| | | | | 24 | 24 | 16 | 16 | 16 | 12 | 12 | 0.6 |
| REPEAT TESTING SHOULD BE PERFORMED FOR ORGANISMS WITH PAIRS OF LSI VALUES IN THIS REGION | | | | | 16 | 16 | 12 | 12 | 8 | 8 | 0.7 |
| | | | | | | 12 | 12 | 8 | 8 | 6 | 0.8 |
| | | | | | | | 8 | 6 | 6 | 6 | 0.9 |
| | | | | | | | | 6 | ≤4 | ≤4 | 1.0 |

MIC = antilog$_2$ {9.97899 exp(-.554 LSI$_3$) - 1.97898 exp(.635 LSI$_{48}$)}

TABLE OF AUTOBAC 1 MIC VALUES

FOR

CEPHALOTHIN VS. STAPHYLOCOCCI

| AUTOBAC 1 LSI FOR 48 MCG DISK (CL/e3) | | | | | | | | | | | AUTOBAC 1 LSI FOR 3 MCG DISK (CL/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >64 | >64 | >64 | >64 | >64 | >64 | >64 | 32 | 24 | 24 | 16 | 0.0 |
| >64 | >64 | >64 | >64 | >64 | >64 | >64 | 24 | 16 | 16 | 12 | 0.1 |
| >64 | >64 | >64 | >64 | >64 | >64 | 64 | 16 | 12 | 12 | 8 | 0.2 |
|  | >64 | >64 | >64 | >64 | 64 | 64 | 8 | 8 | 8 | 6 | 0.3 |
|  |  | >64 | >64 | 64 | 64 | 64 | 8 | 6 | 6 | 4 | 0.4 |
|  |  |  | >64 | 64 | 64 | 64 | 6 | 4 | 4 | 3 | 0.5 |
|  |  |  |  | 64 | 64 | 64 | 4 | 3 | 3 | 2 | 0.6 |
|  |  |  |  |  | 64 | 64 | 3 | 3 | 2 | 2 | 0.7 |
|  |  |  |  |  |  | 48 | 2 | 2 | 2 | 1.5 | 0.8 |
|  |  |  |  |  |  |  | 2 | 1.5 | 1.5 | ≤1 | 0.9 |
|  |  |  |  |  |  |  |  | 1.5 | ≤1 | ≤1 | 1.0 |

REPEAT TESTING SHOULD BE PERFORMED FOR ORGANISMS WITH PAIRS OF LSI VALUES IN THIS REGION

For $LSI_{48} \leq 0.65$ the formula is $MIC = \text{antilog}_2 \{6.2911 \exp(-.14\ LSI_3) + 1.70893 \exp(-4.24\ LSI_{48})\}$ For $LSI_{48} > 0.65$ the formula is $MIC = \text{antilog}_2 \{7.13971 \exp(-.92\ LSI_3) - 1.1004 \exp(.95\ LSI_{48})\}$

TABLE OF AUTOBAC 1 MIC VALUES

FOR

CEPHALOTHIN VS. ENTEROCOCCI

| AUTOBAC 1 LSI FOR 48 MCG DISK (CL/e3) | | | | | | | | | | | AUTOBAC 1 LSI FOR 3 MCG DISK (CL/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >64 | >64 | >64 | >64 | >64 | >64 | >64 | >64 | >64 | 48 | 32 | 0.0 |
| >64 | >64 | >64 | >64 | >64 | >64 | >64 | >64 | 64 | 48 | 32 | 0.1 |
| >64 | >64 | >64 | >64 | >64 | >64 | >64 | >64 | 48 | 32 | 24 | 0.2 |
| | >64 | >64 | >64 | >64 | >64 | >64 | 64 | 48 | 32 | 16 | 0.3 |
| | | >64 | >64 | >64 | >64 | >64 | >64 | 48 | 32 | 24 | 16 | 0.4 |
| | | | >64 | >64 | >64 | >64 | 64 | 48 | 32 | 16 | 12 | 0.5 |
| | | | | >64 | >64 | 48 | 32 | 24 | 16 | 12 | 0.6 |
| | | | | | 64 | 48 | 32 | 16 | 12 | 8 | 0.7 |
| | | | | | | 32 | 24 | 16 | 12 | 6 | 0.8 |
| | | | | | | | 16 | 12 | 8 | 6 | 0.9 |
| | | | | | | | | 8 | 6 | ≤4 | 1.0 |

REPEAT TESTING SHOULD BE PERFORMED FOR ORGANISMS WITH PAIRS OF LSI VALUES IN THIS REGION $$\text{MIC} = \text{antilog}_2 \{832.8[1.0135 \exp(-.00369 \text{ LSI}_3) - \exp(.00725 \text{ LSI}_{48})]\}$$

FIG. 17

FIG. 18
TABLE OF AUTOBAC 1 MIC VALUES
FOR
CEPHALOTHIN VS. ENTEROBACTERIACEAE

| AUTOBAC 1 LSI FOR 48 MCG DISK (CL/e3) | | | | | | | | | | | |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | 0.0 |
| >64 | >64 | >64 | >64 | >64 | >64 | >64 | 64 | 32 | 24 | 12 | 0.1 |
| >64 | >64 | >64 | >64 | >64 | >64 | 64 | 48 | 24 | 16 | 8 | 0.2 |
| >64 | >64 | >64 | >64 | >64 | 64 | 48 | 32 | 24 | 12 | 6 | 0.3 |
|  | 64 | 64 | 64 | 64 | 48 | 48 | 24 | 16 | 8 | 6 | 0.4 |
|  |  | 64 | 64 | 48 | 48 | 32 | 24 | 16 | 8 | 4 | 0.5 |
|  |  |  | 48 | 48 | 32 | 32 | 16 | 12 | 6 | 4 | 0.6 |
|  |  |  |  | 48 | 32 | 24 | 16 | 12 | 6 | 3 | 0.7 |
| REPEAT TESTING SHOULD BE PERFORMED FOR ORGANISMS WITH PAIRS OF LSI VALUES IN THIS REGION |  |  |  |  | 32 | 24 | 16 | 8 | 6 | 3 | 0.8 |
|  |  |  |  |  |  | 24 | 12 | 8 | 4 | 3 | 0.9 |
|  |  |  |  |  |  |  | 12 | 8 | 4 | ≤2 | 1.0 |
|  |  |  |  |  |  |  |  | 8 | 4 | ≤2 |  |

AUTOBAC 1 LSI FOR 3 MCG DISK (CL/e1)

MIC = antilog$_2$ {6.908 − 3.970 LSI$_3$ + 3.064 LSI$_{48}$ + 1.766(LSI$_3$)$^2$ − 6.622(LSI$_{48}$)$^2$}

TABLE OF AUTOBAC 1 MIC VALUES

FOR

CARBENICILLIN VS. PSEUDOMONAS AND ACINETOBACTER SP.

| AUTOBAC 1 LSI FOR 192 MCG DISK (CB/e3) | | | | | | | | | | | |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >256 | >256 | >256 | 256 | 192 | 128 | 96 | 64 | 64* | 64 | 64 | 0.0 |
| >256 | >256 | >256 | 256 | 192 | 128 | 96 | 64 | 48 | 48 | 48 | 0.1 |
| >256 | >256 | >256 | 256 | 192 | 128 | 96 | 64 | 48 | 48 | 48 | 0.2 |
| | >256 | >256 | 256 | 192 | 128 | 96 | 64 | 48 | 32 | 32 | 0.3 |
| | | 256 | 192 | 128 | 96 | 64 | 48 | 32 | 24 | 24 | 0.4 |
| | | | 128 | 96 | 64 | 48 | 32 | 24 | 24 | 24 | 0.5 |
| | | | | 96 | 64 | 48 | 32 | 24 | 16 | 16 | 0.6 |
| REPEAT TESTING SHOULD BE PERFORMED FOR ORGANISMS WITH PAIRS OF LSI VALUES IN THIS REGION | | | | | 48 | 32 | 24 | 16 | 16 | 16 | 0.7 |
| | | | | | 16 | ≤12 | ≤12 | ≤12 | ≤12 | 0.8 |
| | | | | | | ≤12 | ≤12 | ≤12 | ≤12 | 0.9 |
| | | | | | | | ≤12 | ≤12 | ≤12 | 1.0 |

AUTOBAC 1 LSI FOR 12 MCG DISK (CB/e1)

* Equation gives 52 mcg/ml

For $LSI_{192} \leq 0.85$ the equation is MIC = $antilog_2\{9.665 - 4.961(LSI_{192}) - 3.816(LSI_{12})^2\}$ For $LSI_{192} > 0.85$ the equation is MIC = $antilog_2\{5.963 - 3.029(LSI_{12})\}$

TABLE OF AUTOBAC 1 MIC VALUES

FOR

CHLORAMPHENICOL VS. STAPHYLOCOCCI

| AUTOBAC 1 LSI FOR 12 MCG DISK (C/el) | | | | | | | | | | |
|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 |
| >64 | 64 | 48 | 32 | 16 | 12 | 12 | 8 | 6 | 6 | ≤4 |

$\text{MIC} = \text{antilog}_2\{6.894 - 7.873(\text{LSI}_{12}) + 3.216(\text{LSI}_{12})^2\}$

TABLE OF AUTOBAC 1 MIC VALUES

FOR

CHLORAMPHENICOL VS. ENTEROCOCCI

| AUTOBAC 1 LSI FOR 48 MCG DISK (C/e3) | | | | | | | | | | | |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >64 | >64 | >64 | >64 | >64 | >64 | >64 | >64 | >64 | >64 | >64 | 0.0 |
| >64 | >64 | >64 | >64 | >64 | >64 | >64 | >64 | >64 | 64 | 64 | 0.1 |
| >64 | >64 | >64 | >64 | >64 | 64 | 64 | 64 | 64 | 48 | 48 | 0.2 |
| | 64 | 64 | 64 | 64 | 48 | 48 | 48 | 48 | 32 | 32 | 0.3 |
| | | 48 | 48 | 48 | 32 | 32 | 32 | 32 | 24 | 24 | 0.4 |
| | | | 32 | 32 | 24 | 24 | 24 | 24 | 16 | 16 | 0.5 |
| | | | | 24 | 24 | 16 | 16 | 16 | 16 | 12 | 0.6 |
| REPEAT TESTING SHOULD BE PERFORMED FOR ORGANISMS WITH PAIRS OF LSI VALUES IN THIS REGION | | | | | 16 | 12 | 12 | 12 | 12 | 8 | 0.7 |
| | | | | | | 12 | 8 | 8 | 8 | 8 | 0.8 |
| | | | | | | | 6 | 6 | 6 | 6 | 0.9 |
| | | | | | | | ≤4 | ≤4 | ≤4 | ≤4 | 1.0 |

AUTOBAC 1 LSI FOR 12 MCG DISK (C/e1)

MIC = antilog$_2$ {11.67[1.67218 exp(-.27 LSI$_{12}$)-exp(.10 LSI$_{48}$)]}

TABLE OF AUTOBAC 1 MIC VALUES

FOR

CHLORAMPHENICOL VS. ENTEROBACTERIACEAE

| AUTOBAC 1 LSI FOR 48 MCG DISK (C/e3) | | | | | | | | | | | |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >64 | >64 | >64 | >64 | 64 | 64 | 48 | 48 | 48 | 32 | 32 | 0.0 |
| >64 | >64 | >64 | >64 | 64 | 64 | 48 | 48 | 48 | 32 | 32 | 0.1 |
| >64 | >64 | >64 | 64 | 64 | 64 | 48 | 48 | 32 | 32 | 32 | 0.2 |
| | >64 | >64 | 64 | 64 | 48 | 48 | 48 | 32 | 32 | 24 | 0.3 |
| | | 64 | 64 | 48 | 48 | 48 | 32 | 32 | 24 | 24 | 0.4 |
| | | | 48 | 48 | 48 | 32 | 32 | 24 | 24 | 24 | 0.5 |
| | | | | 48 | 32 | 32 | 24 | 24 | 16 | 16 | 0.6 |
| REPEAT TESTING SHOULD BE PERFORMED FOR ORGANISMS WITH PAIRS OF LSI VALUES IN THIS REGION | | | | | 32 | 24 | 24 | 16 | 16 | 12 | 0.7 |
| | | | | | | 16 | 16 | 16 | 12 | 12 | 0.8 |
| | | | | | | | 12 | 12 | 8 | 8 | 0.9 |
| | | | | | | | | 8 | 8 | ≤6 | 1.0 |

AUTOBAC 1 LSI FOR 12 MCG DISK (C/e1)

MIC = antilog$_2$ {6.973−2.035(LSI$_{48}$)−2.341(LSI$_{12}$)$^2$}

TABLE OF AUTOBAC 1 MIC VALUES

FOR

CHLORAMPHENICOL VS. PSEUDOMONAS AND ACINETOBACTER SP.

| AUTOBAC 1 LSI FOR 48 MCG DISK (C/e3) | | | | | | | | | | | AUTOBAC 1 LSI FOR 12 MCG DISK (C/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >64 | >64 | >64 | >64 | >64 | >64 | >64 | >64 | 64 | 64 | | 0.0 |
| >64 | >64 | >64 | >64 | >64 | >64 | >64 | >64 | 64 | 64 | | 0.1 |
| >64 | >64 | >64 | >64 | >64 | >64 | >64 | 64 | 64 | 64 | | 0.2 |
| | >64 | >64 | >64 | >64 | >64 | >64 | >64 | 64 | 64 | 48 | 0.3 |
| | | >64 | >64 | >64 | >64 | >64 | 64 | 64 | 48 | 48 | 0.4 |
| | | | >64 | 64 | 64 | 64 | 64 | 48 | 48 | 32 | 0.5 |
| | | | | 64 | 64 | 48 | 48 | 48 | 32 | 32 | 0.6 |
| REPEAT TESTING SHOULD BE PERFORMED FOR ORGANISMS WITH PAIRS OF LSI VALUES IN THIS REGION | | | | | 48 | 48 | 32 | 32 | 24 | 24 | 0.7 |
| | | | | | | 32 | 24 | 24 | 24 | 16 | 0.8 |
| | | | | | | | 16 | 16 | 16 | 12 | 0.9 |
| | | | | | | | | 12 | 12 | ≤8 | 1.0 |

MIC = antilog$_2$ {7.143 − 2.870(LSI$_{12}$)$^2$ − 1.161(LSI$_{48}$)$^2$}

FIG. 23

FIG. 24
TABLE OF AUTOBAC 1 MIC VALUES

FOR

CLINDAMYCIN VS. STAPHYLOCOCCI

| AUTOBAC 1 LSI FOR 6 MCG DISK (CM/e3) | | | | | | | | | | | |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >8 | >8 | 8 | 6 | 4 | 3 | 2 | 2 | 1.5 | 1 | .75 | 0.0 |
| >8 | >8 | 8 | 6 | 4 | 3 | 2 | 1.5 | 1.5 | 1 | .75 | 0.1 |
| >8 | >8 | 8 | 6 | 4 | 3 | 2 | 1.5 | 1 | 1 | .75 | 0.2 |
| | >8 | 8 | 6 | 4 | 3 | 2 | 1.5 | 1 | .75 | ≤.5 | 0.3 |
| | | 8 | 6 | 4 | 3 | 2 | 1.5 | 1 | .75 | ≤.5 | 0.4 |
| | | | 6 | 4 | 3 | 2 | 1.5 | 1 | .75 | ≤.5 | 0.5 |
| | | | | 4 | 3 | 2 | 1.5 | 1 | .75 | ≤.5 | 0.6 |
| REPEAT TESTING SHOULD BE PERFORMED FOR ORGANISMS WITH PAIRS OF LSI VALUES IN THIS REGION | | | | | 3 | 2 | 1.5 | 1 | .75 | ≤.5 | 0.7 |
| | | | | | | 2 | 1.5 | 1 | .75 | ≤.5 | 0.8 |
| | | | | | | | 1.5 | 1 | .75 | ≤.5 | 0.9 |
| | | | | | | | | 1 | .75 | ≤.5 | 1.0 |

AUTOBAC 1 LSI FOR 1.5 MCG DISK (CM/e1)

MIC = antilog$_2$ {89.31[1.04479·exp(−.00452 LSI$_{1.5}$)−exp(.05 LSI$_6$)]}

TABLE OF AUTOBAC 1 MIC VALUES

FOR

GENTAMICIN VS. STAPHYLOCOCCI

| AUTOBAC 1 LSI FOR 12 MCG DISK (GM/e3) | | | | | | | | | | | AUTOBAC 1 LSI FOR 3 MCG DISK (GM/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| ≥16 | 16 | 16 | 16 | 16 | 16 | 16 | 16 | 12 | 12 | 12 | 0.0 |
| 8 | 8 | 8 | 8 | 8 | 8 | 8 | 8 | 8 | 8 | 8 | 0.1 |
| 6 | 6 | 6 | 6 | 6 | 6 | 6 | 6 | 6 | 4 | 4 | 0.2 |
|   | 4 | 4 | 4 | 4 | 4 | 4 | 4 | 3 | 3 | 3 | 0.3 |
|   |   | 3 | 3 | 3 | 3 | 3 | 3 | 3 | 2 | 2 | 0.4 |
|   |   |   | 2 | 2 | 2 | 2 | 2 | 2 | 2 | 2 | 0.5 |
|   |   |   |   | 2 | 2 | 2 | 2 | 1.5 | 1.5 | 1.5 | 0.6 |
| REPEAT TESTING SHOULD BE PERFORMED FOR ORGANISMS WITH PAIRS OF LSI VALUES IN THIS REGION | | | | | 1.5 | 1.5 | 1.5 | 1.5 | 1.5 | 1.5 | 0.7 |
| | | | | | | 1.5 | 1.5 | 1.5 | 1.5 | ≤1 | 0.8 |
| | | | | | | | 1.5 | ≤1 | ≤1 | ≤1 | 0.9 |
| | | | | | | | | ≤1 | ≤1 | ≤1 | 1.0 |

MIC = antilog$_2$ {4.03909 exp(-2.278 LSI$_3$) - .0390864 exp(2.360 LSI$_{12}$)}

TABLE OF AUTOBAC 1 MIC VALUES

FOR

GENTAMICIN VS. ENTEROBACTERIACEAE

| AUTOBAC 1 LSI FOR 12 MCG DISK (GM/e3) | | | | | | | | | | | AUTOBAC 1 LSI FOR 3 MCG DISK (GM/e3) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| ≥16 | 16 | 14 | 12 | 12 | 10 | 10 | 8 | 8 | 7 | 7 | 0.0 |
| 12 | 12 | 10 | 10 | 8 | 8 | 7 | 6 | 6 | 5 | 5 | 0.1 |
| 10 | 8 | 8 | 7 | 6 | 6 | 5 | 5 | 4 | 4 | 3.5 | 0.2 |
| | 6 | 6 | 5 | 5 | 4 | 4 | 3.5 | 3.5 | 3 | 3 | 0.3 |
| | | 5 | 4 | 4 | 3.5 | 3.5 | 3 | 2.5 | 2.5 | 2.5 | 0.4 |
| | | | 3.5 | 3 | 3 | 2.5 | 2.5 | 2 | 2 | 1.75 | 0.5 |
| | | | | 2.5 | 2.5 | 2.5 | 2 | 1.75 | 1.75 | 1.5 | 0.6 |
| REPEAT TESTING SHOULD BE PERFORMED FOR ORGANISMS WITH PAIRS OF LSI VALUES IN THIS REGION | | | | | 2 | 2 | 1.75 | 1.75 | 1.5 | 1.25 | 0.7 |
| | | | | | | 1.75 | 1.5 | 1.5 | 1.25 | 1.25 | 0.8 |
| | | | | | | | 1.5 | 1.25 | 1.25 | ≤1 | 0.9 |
| | | | | | | | | 1.25 | 1.25 | ≤1 | 1.0 |

MIC = $\text{antilog}_2 \{4.067 - 4.756(LSI_3) - 1.338(LSI_{12}) + 2.108(LSI_3)^2\}$

TABLE OF AUTOBAC 1 MIC VALUES

FOR

GENTAMICIN VS. PSEUDOMONAS AND ACINETOBACTER SP.

| AUTOBAC 1 LSI FOR 12 MCG DISK (GM/e3) | | | | | | | | | | | AUTOBAC 1 LSI FOR 3 MCG DISK (GM/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >16 | >16 | >16 | >16 | >16 | 16 | 16 | 16 | 12 | 12 | 12 | 0.0 |
| >16 | >16 | >16 | >16 | >16 | 16 | 16 | 16 | 12 | 12 | 12 | 0.1 |
| >16 | >16 | >16 | >16 | 16 | 16 | 16 | 12 | 12 | 12 | 12 | 0.2 |
| | >16 | >16 | >16 | 16 | 16 | 16 | 12 | 12 | 12 | 8 | 0.3 |
| | | 16 | 16 | 16 | 16 | 12 | 12 | 12 | 8 | 8 | 0.4 |
| | | | 16 | 12 | 12 | 12 | 8 | 8 | 8 | 6 | 0.5 |
| | | | | 12 | 8 | 8 | 8 | 6 | 6 | 6 | 0.6 |
| REPEAT TESTING SHOULD BE PERFORMED FOR ORGANISMS WITH PAIRS OF LSI VALUES IN THIS REGION | | | | | 8 | 6 | 6 | 6 | 4 | 4 | 0.7 |
| | | | | | | 6 | 4 | 4 | 4 | 3 | 0.8 |
| | | | | | | | 3 | 3 | 3 | ≤2 | 0.9 |
| | | | | | | | ≤2 | ≤2 | ≤2 | | 1.0 |

MIC = antilog$_2$ {5.052−2.689(LSI$_3$)$^2$−1.636(LSI$_{12}$)}

FIG. 27

FIG. 28
TABLE OF AUTOBAC 1 MIC VALUES
FOR
KANAMYCIN VS. ENTEROBACTERIACEAE

| AUTOBAC 1 LSI FOR 24 MCG DISK (K/e3) | | | | | | | | | | | AUTOBAC 1 LSI FOR 6 MCG DISK (K/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >32 | >32 | 32 | 24 | 16 | 12 | 12 | 8 | 6 | 6 | 6 | 0.0 |
| >32 | >32 | 32 | 16 | 16 | 12 | 8 | 6 | 6 | 6 | 4 | 0.1 |
| >32 | 32 | 24 | 16 | 12 | 8 | 8 | 6 | 6 | 4 | 4 | 0.2 |
| | 32 | 24 | 16 | 12 | 8 | 6 | 6 | 4 | 4 | 4 | 0.3 |
| | | 16 | 12 | 8 | 6 | 6 | 4 | 4 | 3 | 3 | 0.4 |
| | | | 12 | 8 | 6 | 4 | 4 | 3 | 3 | 3 | 0.5 |
| | | | | 8 | 6 | 4 | 4 | 3 | 3 | 3 | 0.6 |
| REPEAT TESTING SHOULD BE PERFORMED FOR ORGANISMS WITH PAIRS OF LSI VALUES IN THIS REGION | | | | | 6 | 4 | 3 | 3 | 3 | ≤2 | 0.7 |
| | | | | | | 4 | 3 | 3 | 3 | ≤2 | 0.8 |
| | | | | | | | 3 | 3 | ≤2 | ≤2 | 0.9 |
| | | | | | | | | 3 | ≤2 | ≤2 | 1.0 |

MIC = antilog$_2$ {6.295−2.747(LSI$_6$)+1.361(LSI$_6$)$^2$−6.766(LSI$_{24}$)+2.993(LSI$_{24}$)$^2$}

TABLE OF AUTOBAC 1 MIC VALUES

FOR

KANAMYCIN VS. PSEUDOMONAS AND ACINETOBACTER SP.

| AUTOBAC 1 LSI FOR 24 MCG DISK (CM/e3) | | | | | | | | | | | AUTOBAC 1 LSI FOR 6 MCG DISK (CM/e3) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >32 | >32 | >32 | >32 | >32 | >32 | >32 | >32 | 32 | 32 | 24 | 0.0 |
| >32 | >32 | >32 | >32 | >32 | 32 | 32 | 32 | 24 | 24 | 24 | 0.1 |
| >32 | >32 | >32 | 32 | 32 | 32 | 24 | 24 | 16 | 16 | 16 | 0.2 |
| | 32 | 32 | 24 | 24 | 24 | 16 | 16 | 16 | 12 | 12 | 0.3 |
| | | 24 | 24 | 16 | 16 | 16 | 12 | 12 | 8 | 8 | 0.4 |
| | | | 16 | 12 | 12 | 12 | 8 | 8 | 8 | 6 | 0.5 |
| | | | | 12 | 8 | 8 | 8 | 6 | 6 | 6 | 0.6 |
| REPEAT TESTING SHOULD BE PERFORMED FOR ORGANISMS WITH PAIRS OF LSI VALUES IN THIS REGION | | | | | 8 | 6 | 6 | 6 | 4 | 4 | 0.7 |
| | | | | | | 6 | 4 | 4 | 4 | 3 | 0.8 |
| | | | | | | | 4 | 3 | 3 | 3 | 0.9 |
| | | | | | | | | 3 | ≤2 | ≤2 | 1.0 |

MIC = antilog$_2$ {11.4402 exp(−.4 LSI$_6$) − 4.94023 exp(.3 LSI$_{24}$)}

FIG. 29

FIG. 30
TABLE OF AUTOBAC 1 MIC VALUES

FOR

METHICILLIN VS. STAPHYLOCOCCI

| AUTOBAC 1 LSI FOR 12 MCG DISK (SC/e3) | | | | | | | | | | | AUTOBAC 1 LSI FOR 3 MCG DISK (SC/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >16 | >16 | >16 | >16 | >16 | >16 | 16 | 12 | 12 | 8 | 6 | 0.0 |
| >16 | >16 | >16 | >16 | >16 | 16 | 16 | 12 | 8 | 8 | 6 | 0.1 |
| >16 | >16 | >16 | 16 | 16 | 16 | 12 | 12 | 8 | 6 | 4 | 0.2 |
| | 16 | 16 | 16 | 16 | 12 | 12 | 8 | 6 | 6 | 4 | 0.3 |
| | | 16 | 16 | 12 | 12 | 8 | 8 | 6 | 4 | 3 | 0.4 |
| | | | 12 | 12 | 8 | 8 | 6 | 6 | 4 | 3 | 0.5 |
| | | | | 8 | 8 | 6 | 6 | 4 | 3 | 2 | 0.6 |
| REPEAT TESTING SHOULD BE PERFORMED FOR ORGANISMS WITH PAIRS OF LSI VALUES IN THIS REGION | | | | | 8 | 6 | 4 | 4 | 3 | 2 | 0.7 |
| | | | | | | 6 | 4 | 3 | 2 | 2 | 0.8 |
| | | | | | | | 4 | 3 | 2 | ≤1.5 | 0.9 |
| | | | | | | | | 2 | 2 | ≤1.5 | 1.0 |

MIC = antilog$_2$ {4.918 − 2.178(LSI$_3$) − 2.337(LSI$_{12}$)$^2$}

FIG. 30

FIG. 31
TABLE OF AUTOBAC 1 MIC VALUES
FOR
PENICILLIN G VS. STAPHYLOCOCCI

| AUTOBAC 1 LSI FOR 48 UNIT DISK (P/e4) | | | | | | | | | | | AUTOBAC 1 LSI FOR 0.188 UNIT DISK (P/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| ≥64 | 32 | 32 | 16 | 16 | 8 | 8 | 4 | 4 | 2 | 2 | 0.0 |
| 32 | 32 | 16 | 16 | 8 | 8 | 4 | 4 | 2 | 2 | 1 | 0.1 |
| 32 | 16 | 16 | 8 | 8 | 4 | 4 | 2 | 2 | 1 | 1 | 0.2 |
|  | 16 | 8 | 8 | 4 | 4 | 2 | 2 | 1 | 1 | 0.5 | 0.3 |
|  |  | 8 | 4 | 4 | 2 | 2 | 1 | 1 | 0.5 | 0.5 | 0.4 |
|  |  |  | 4 | 2 | 2 | 1 | 1 | 0.5 | 0.5 | 0.25 | 0.5 |
|  |  |  |  | 2 | 1 | 1 | 0.5 | 0.5 | 0.25 | 0.25 | 0.6 |
|  |  |  |  |  | 1 | 0.5 | 0.5 | 0.25 | 0.25 | 0.125 | 0.7 |
|  |  |  |  |  | 0.5 | 0.25 | 0.25 | 0.125 | 0.125 | 0.8 |
|  |  |  |  |  |  |  | 0.125 | 0.125 | 0.125 | ≤0.063 | 0.9 |
|  |  |  |  |  |  |  |  | ≤0.063 | ≤0.063 | ≤0.063 | 1.0 |

REPEAT TESTING SHOULD BE PERFORMED FOR ORGANISMS WITH PAIRS OF LSI VALUES IN THIS REGION $$MIC = \text{antilog}_2 \{11.33[-\exp(.385\ LSI_{.188}) + 1.51151\ \exp(-.343\ LSI_{48})]\}$$

TABLE OF AUTOBAC 1 MIC VALUES

FOR

PENICILLIN G VS. ENTEROCOCCI

| AUTOBAC 1 LSI FOR 48 UNIT DISK (P/e4) | | | | | | | | | | | AUTOBAC 1 LSI FOR 12 UNIT DISK (P/e3) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >64 | >64 | >64 | >64 | >64 | >64 | >64 | >64 | >64 | >64 | >64 | 0.0 |
| >64 | >64 | >64 | >64 | >64 | >64 | >64 | >64 | >64 | >64 | 64 | 0.1 |
| >64 | >64 | >64 | >64 | >64 | >64 | >64 | 64 | 64 | 64 | 48 | 0.2 |
|  | >64 | >64 | >64 | >64 | 64 | 64 | 48 | 48 | 32 | 32 | 0.3 |
|  |  | 64 | 64 | 64 | 48 | 48 | 32 | 32 | 24 | 24 | 0.4 |
|  |  |  | 48 | 48 | 32 | 32 | 24 | 24 | 24 | 16 | 0.5 |
|  |  |  |  | 32 | 24 | 24 | 24 | 16 | 16 | 12 | 0.6 |
|  |  |  |  |  | 24 | 16 | 16 | 12 | 12 | 8 | 0.7 |
|  |  |  |  |  |  | 12 | 12 | 8 | 8 | 6 | 0.8 |
|  |  |  |  |  |  |  | 8 | 8 | 6 | 6 | 0.9 |
|  |  |  |  |  |  |  |  | 6 | ≤4 | ≤4 | 1.0 |

REPEAT TESTING SHOULD BE PERFORMED FOR ORGANISMS WITH PAIRS OF LSI VALUES IN THIS REGION

MIC = antilog$_2$ {11.9148 exp(-.5 LSI$_{12}$) - 3.17015 exp(.5 LSI$_{48}$)}

FIG. 32

FIG. 33
TABLE OF AUTOBAC 1 MIC VALUES
FOR
PENICILLIN VS. ENTEROBACTERIACEAE

| AUTOBAC 1 LSI FOR 48 UNIT DISK (P/e4) | | | | | | | | | | | |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >64 | >64 | >64 | 64 | 64 | 64 | 48 | 48 | 32 | 32 | 24 | 0.0 |
| >64 | >64 | >64 | 64 | 64 | 64 | 48 | 48 | 32 | 32 | 24 | 0.1 |
| >64 | >64 | >64 | 64 | 64 | 48 | 48 | 32 | 32 | 32 | 24 | 0.2 |
| | >64 | 64 | 64 | 48 | 48 | 48 | 32 | 32 | 24 | 24 | 0.3 |
| | | 64 | 48 | 48 | 48 | 32 | 32 | 24 | 24 | 16 | 0.4 |
| | | | 48 | 32 | 32 | 32 | 24 | 24 | 16 | 16 | 0.5 |
| | | | | 32 | 24 | 24 | 16 | 16 | 12 | 12 | 0.6 |
| REPEAT TESTING SHOULD BE PERFORMED FOR ORGANISMS WITH PAIRS OF LSI VALUES IN THIS REGION | | | | | 16 | 16 | 16 | 12 | 12 | 8 | 0.7 |
| | | | | | | 12 | 12 | 8 | 8 | 6 | 0.8 |
| | | | | | | | 6 | 6 | 6 | 4 | 0.9 |
| | | | | | | | | 4 | ≤3 | ≤3 | 1.0 |

AUTOBAC 1 LSI FOR 12 UNIT DISK (P/e3)

$$MIC = \text{antilog}_2 \{6.972 - 2.252(LSI_{48}) - 3.214(LSI_{12})^2\}$$

FIG. 33

FIG. 34
TABLE OF AUTOBAC I MIC VALUES
FOR
TETRACYCLINE VS. STAPHYLOCOCCI

| AUTOBAC I LSI FOR 12 MCG DISK (TE/e3) | | | | | | | | | | | AUTOBAC I LSI FOR 3 MCG DISK (TE/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >16 | >16 | >16 | >16 | >16 | >16 | >16 | >16 | >16 | >16 | >16 | 0.0 |
| >16 | >16 | >16 | >16 | >16 | >16 | >16 | >16 | >16 | >16 | >16 | 0.1 |
| 16 | 16 | 16 | 16 | 16 | 16 | 16 | 16 | 16 | 16 | 12 | 0.2 |
|  | 8 | 8 | 8 | 8 | 8 | 8 | 8 | 8 | 8 | 8 | 0.3 |
|  |  | 6 | 6 | 6 | 6 | 6 | 6 | 6 | 4 | 4 | 0.4 |
|  |  |  | 4 | 4 | 3 | 3 | 3 | 3 | 3 | 3 | 0.5 |
|  |  |  |  | 2 | 2 | 2 | 2 | 2 | 2 | 2 | 0.6 |
| REPEAT TESTING SHOULD BE PERFORMED FOR ORGANISMS WITH PAIRS OF LSI VALUES IN THIS REGION |  |  |  |  | 1.5 | 1.5 | 1.5 | 1.5 | 1.5 | 1.5 | 0.7 |
|  |  |  |  |  |  | ≤1 | ≤1 | ≤1 | ≤1 | ≤1 | 0.8 |
|  |  |  |  |  |  |  | ≤1 | ≤1 | ≤1 | ≤1 | 0.9 |
|  |  |  |  |  |  |  |  | ≤1 | ≤1 | ≤1 | 1.0 |

MIC = antilog$_2$ {8.60602 exp(-1.295 LSI$_3$)-2.60604 exp(.092 LSI$_{12}$)}

TABLE OF AUTOBAC 1 MIC VALUES

FOR

TETRACYCLINE VS. ENTEROCOCCI

| AUTOBAC 1 LSI FOR 12 MCG DISK (TE/e3) | | | | | | | | | | | |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >16 | >16 | >16 | >16 | >16 | >16 | >16 | >16 | >16 | >16 | >16 | 0.0 |
| >16 | >16 | >16 | >16 | >16 | >16 | >16 | >16 | >16 | >16 | >16 | 0.1 |
| 16 | 16 | 16 | 16 | 16 | 16 | 16 | 12 | 12 | 12 | 12 | 0.2 |
| | 8 | 8 | 8 | 8 | 8 | 8 | 8 | 8 | 8 | 8 | 0.3 |
| | | 6 | 6 | 6 | 6 | 6 | 6 | 6 | 6 | 6 | 0.4 |
| | | | 4 | 4 | 4 | 4 | 4 | 4 | 4 | 4 | 0.5 |
| | | | | 3 | 3 | 3 | 3 | 3 | 3 | 3 | 0.6 |
| REPEAT TESTING SHOULD BE PERFORMED FOR ORGANISMS WITH PAIRS OF LSI VALUES IN THIS REGION | | | | | 2 | 2 | 2 | 2 | 2 | 2 | 0.7 |
| | | | | | | 1.5 | 1.5 | 1.5 | 1.5 | 1.5 | 0.8 |
| | | | | | | | 1.5 | 1.5 | 1.5 | 1.5 | 0.9 |
| | | | | | | | | ≤1 | ≤1 | ≤1 | 1.0 |

AUTOBAC 1 LSI FOR 3 MCG DISK (TE/e1)

MIC = antilog$_2$ {8.01149 exp(-1.06 LSI$_3$) - 2.5115 exp(.1 LSI$_{12}$)}

TABLE OF AUTOBAC 1 MIC VALUES

FOR

TETRACYCLINE VS. ENTEROBACTERIACEAE

| AUTOBAC 1 LSI FOR 12 MCG DISK (TE/e3) | | | | | | | | | | | AUTOBAC 1 LSI FOR 3 MCG DISK (TE/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >16 | >16 | >16 | >16 | >16 | >16 | >16 | >16 | >16 | >16 | >16 | 0.0 |
| >16 | >16 | >16 | >16 | >16 | >16 | >16 | >16 | >16 | >16 | >16 | 0.1 |
| >16 | >16 | >16 | >16 | >16 | >16 | >16 | 16 | 16 | 16 | 16 | 0.2 |
| | 16 | 16 | 16 | 16 | 16 | 16 | 16 | 12 | 12 | 12 | 0.3 |
| | | 12 | 12 | 12 | 12 | 12 | 12 | 12 | 12 | 12 | 0.4 |
| | | | 8 | 8 | 8 | 8 | 8 | 8 | 8 | 8 | 0.5 |
| | | | | 6 | 6 | 6 | 6 | 6 | 6 | 6 | 0.6 |
| REPEAT TESTING SHOULD BE PERFORMED FOR ORGANISMS WITH PAIRS OF LSI VALUES IN THIS REGION | | | | | 4 | 4 | 4 | 4 | 4 | 4 | 0.7 |
| | | | | | | 4 | 4 | 4 | 4 | 4 | 0.8 |
| | | | | | | | 3 | 3 | 3 | 3 | 0.9 |
| | | | | | | | | 3 | 3 | ≤2 | 1.0 |

MIC = antilog$_2$ {7.34428 exp(-.79 LSI$_3$) - 1.84429 exp(.0975 LSI$_{12}$)}

TABLE OF AUTOBAC 1 MIC VALUES

FOR

TETRACYCLINE VS. PSEUDOMONAS AND ACINETOBACTER SP.

| AUTOBAC 1 LSI FOR 12 MCG DISK (TE/e3) | | | | | | | | | | | AUTOBAC 1 LSI FOR 3 MCG DISK (TE/e1) |
|---|---|---|---|---|---|---|---|---|---|---|---|
| 0.0 | 0.1 | 0.2 | 0.3 | 0.4 | 0.5 | 0.6 | 0.7 | 0.8 | 0.9 | 1.0 | |
| >16 | >16 | >16 | >16 | >16 | >16 | >16 | >16 | 16 | 16 | 12 | 0.0 |
| >16 | >16 | >16 | >16 | >16 | >16 | >16 | 16 | 16 | 12 | 12 | 0.1 |
| >16 | >16 | >16 | >16 | >16 | >16 | >16 | 16 | 16 | 12 | 12 | 0.2 |
| | >16 | >16 | >16 | >16 | >16 | 16 | 16 | 16 | 12 | 8 | 0.3 |
| | | >16 | >16 | >16 | 16 | 16 | 16 | 12 | 12 | 8 | 0.4 |
| | | | 16 | 16 | 16 | 16 | 12 | 12 | 8 | 6 | 0.5 |
| | | | | 16 | 12 | 12 | 8 | 8 | 6 | 6 | 0.6 |
| REPEAT TESTING SHOULD BE PERFORMED FOR ORGANISMS WITH PAIRS OF LSI VALUES IN THIS REGION | | | | | 8 | 8 | 8 | 6 | 6 | 4 | 0.7 |
| | | | | | | 6 | 6 | 4 | 4 | 3 | 0.8 |
| | | | | | | | 4 | 3 | 3 | 2 | 0.9 |
| | | | | | | | | 2 | 2 | ≤1.5 | 1.0 |

MIC = antilog$_2$ {5.126−2.902(LSI$_3$)$^2$−1.629(LSI$_{12}$)$^2$}

FIG. 37

METHOD AND APPARATUS FOR DETERMINING THE MINIMUM CONCENTRATION OF ANTIBIOTIC NECESSARY TO AT LEAST INHIBIT MICROORGANISM GROWTH

This invention deals generally with methods and apparatus for determining the minimum concentration of a predetermined antibiotic (or other antimicrobial agents) necessary to at least inhibit the activity of sampled pathogenic microorganisms taken from a predetermined general class of such organisms. In particular, the exemplary embodiment deals with method and apparatus for determining the minimum inhibitory concentration (MIC) for given combinations of antibiotic and general classes of microorganisims. However, there are other minimum concentration measurements such as minimum bactericidal concentration (MBC) or minimum lethal concentration (MLC) which are often desired and for which the same general techniques of this invention may be useful.

Many antibiotic substances produce undesirable side effects or become toxic or otherwise disadvantageous when given in sufficiently high dosage to particular patients and/or under particular medical circumstances. Therefore, it is often very desirable for a doctor to have some indication of the minimum concentration of a given antibiotic necessary to at least inhibit the activity of the pathogenic microorganisms involved in the patient's illness. However, while there are several accepted quantitative laboratory techniques for determining factors such as MIC, it is estimated that such procedures are only attempted in approximately 20% of the situations where such information would be highly desirable. Failure to determine MIC in so many instances where it would be beneficial to have such information is believed to be caused by the many difficult practical and economic problems now associated with conventional techniques for determining MIC.

For example, there are the broth dilution, agar dilution, and agar diffusion methods of determining MIC. (See Ericsson et al, *Antibiotic Sensitivity Testing, Report of an International Collaborative Study*, Acta Pathologica et Microbiologica Scandinavica, Section B 1971, Supplement No. 217, Section 2.1 entitled "Basic Methods and Media Employed"). The broth and agar dilution methods both utilize a series of separate containers of microorganism growth media. Each successive container has a different respectively corresponding concentration of a predetermined antibiotic and the microorganism in question is placed into all of the containers. After a suitable incubation period (on the order of 16-20 hours, for example) these series of containers are visually checked and classified as containing either "growth" or "no growth". The minimum antibiotic concentration existing in the containers which have been classified as having "no growth" is then taken as the minimum inhibitory concentration (MIC) for that particular combination of antibiotic and microorganism. However, since the antibiotic concentrations generally vary by two-fold dilutions from one container to the next in the series, the precision of such an MIC determination may be quite poor. Even if the operators' visual inspection and determination of "no growth" is correct, the actual MIC may be considerably higher or lower than the determined MIC.

There are also many practical and economic problems involved in using such dilution techniques for routine determination of MIC in a hospital laboratory environment. For example, the task of accurately preparing serial dilutions of antibiotic in a suitable growth medium, the requirement to incubate such a large number of different samples for long time periods and the necessity to manually inspect and judge each of the containers, all present vey difficult problems when one attempts to perform measurements on a routine basis for many patients, microorganisms and antibiotics.

The agar diffusion method (See Bauer et al, "Antibiotic Susceptibility Testing by a Standardized Single Disk Method", Am. J. Clin. Path. 45: 493-496, 1966) involves the placement of an antibiotic containing disc on the surface of an agar medium earlier inoculated with the microorganism in question. The antibiotic substance then diffuses away from the disc such that the effective concentration of antibiotic in the growth medium varies as a function of the radius from the disc. Thus, at least theoretically, the diameter of a resulting "no growth" area about the antibiotic disc should be proportional, or at least related in some functional manner, to the MIC. However, in a practical hospital laboratory environment, there are difficulties with this technique because the diameter of the "no growth" area also depends on many other factors.

There have been several prior attempts to minimize the practical and economic problems involved with the serial dilution techniques for determining MIC. For example, Dr. John A. Washington II at Mayo Clinic (See, for example, Washington, et al, *Manual of Clinical Microbiology*, 2nd Edition, American Society for Microbiology, 1974, Chapter 45 entitled: "Dilution Test Procedures" and *Current Techniques for Antibiotic Susceptibility Testing*, published by Charles C. Thomas, 1974, Chapter VI entitled "The Agar-Dilution Technique") has tried to minimize the number of dilutions used by using only the dilution levels which are approximately achievable within the human body. The resulting dilution series still required many separate containers for each MIC determination although Dr. Washington is believed to have sometimes used smaller or larger dilution intervals between successive containers in an effort to minimize the number of tubes involved.

Dr. Yves Chabbert (Pasteur Institute) in France has attempted to make the serial dilution technique more precise and accurate by making the dilution intervals smaller. For example, he has used dilution intervals of approximately 1.25 rather than the usual two-fold dilution technique. However, such smaller dilution intervals not only increase the number of containers involved, they also make the visual judgment of growth or no growth in adjacent tubes more difficult since there may be gradually declining rates of growth in a number of adjacent tubes. This difficulty is sometimes known as the diffuse end point problem.

Others have also tried to improve the accepted MIC measurement techniques by miniaturization, automation or semiautomation of the several physical processes required. For example, a device known as the Steers' replicator can be used for simultaneously inoculating a matrix of 36 sites on an agar plate with 36 respectively corresponding different microorganisms. Dynatech Corporation (Cooke Division) offers equipment to help automate and/or miniaturize the MIC determination with equipment to automatically pump antibiotic solutions of various concentrations into a matrix of wells. Micro-Media Systems, Inc. in California provides frozen prepared broth dilution plates having predetermined concentrations of antibiotics. Others no doubt also provide services and/or equipment to help minimize the practical problems encountered with the routine hospital laboratory use of either broth or agar dilution MIC measurements.

Of course there are also well accepted methods and apparatus in the prior art for qualitative determinations of susceptibility of given microorganisms to given antibiotics. For example, the Autobac 1 Interpretative Susceptibility (AIS) Test System (see U.S. Pat. No. 3,832,532—Praglin et al, 1974 and McGowan, Jr., et al, "Rapid Semiquantitative Testing of Antibiotic Susceptibility: Use of a Multicell Disk Elution System;" *Antimicrobial and Chemotherapy,* May 1974, pp. 543–548) is available from Pfizer Diagnostics, a division of Pfizer Inc. This system automatically measures the growth of a given microorganism in a liquid broth growth medium in the presence of predetermined concentrations of various antibiotics. The concentrations are predetermined such that growth readings on either side of a predetermined fixed break point are interpreted as meaning "susceptibility" or "lack of susceptibility" respectively to the given antibiotic. Accordingly, this type of system has been used heretofore for only qualitative measurements as opposed to quantitative measurements such as MIC. Of course, it would be possible to use such systems to assist in the traditional serial dilution scheme of quantitatively measuring an MIC or to confirm a given MIC once it has otherwise been determined. A similar system has also been described in U.S. Pat. No. 3,837,745—Acker et al (1974).

The present invention involves a modification in the method and apparatus previously employed by the Autobac 1 system so that accurate quantitative measurements of MIC may be rapidly provided in a typical medical laboratory environment and in an economical, practical way. With this invention, only a very few (e.g. one or two) actual measurements of microorganism growth need be made to determine actual MIC in a precise and accurate way in spite of the fact that relatively brief (e.g. 5 hours) incubation times are involved. In fact, the technique is, at least in part, made possible by taking growth measurements at a relatively early stage before the growth levels have saturated at the traditional "growth" or "no growth" extremes.

In brief, it has been discovered that a fixed functional relationship (in either tabular or equation form) may be established between MIC and microorganism growth for a few (e.g. one or two) predetermined concentrations of a given antibiotic. This initial establishment of a predetermined functional relationship is carried out in advance using accepted quantatitive measurement procedures and accepted regression analysis techniques. Even though such an initial procedure itself may be time consuming, once the functional relationship has been established, the actual determination of MIC for any given microorganism taken from the same general class may be determined quickly and simply by measuring the growth of that microorganism in the same few (e.g., one or two) predetermined concentrations of the antibiotic in question and then using such measurements with the preestablished functional relationship to determine the MIC. Experience has shown that the MIC value determined in this way is usually at least as precise and accurate (if not more so) than previously accepted MIC measurement techniques. At the same time, this procedure provides the MIC value much more quickly, conveniently and economically than has heretofore been thought possible.

To help achieve the desired results with this invention, care is also taken to insure accurate predetermined concentrations of antibiotic within the broth growth medium. Furthermore, the broth itself has been designed so as to enhance rapid growth (and thus reduce the time required for an MIC determination) and also to enhance the optical purity of the liquid broth, since, in the exemplary embodiment, growth measurements are made by detecting scattered light passing through the broth.

These and other objects and advantages of this invention will be more completely apparent from the following detailed description of the presently preferred exemplary embodiment of the invention taken in conjunction with the accompanying drawings, of which:

FIG. 1 is a schematic depiction of the process involved in the presently preferred exemplary embodiment of this invention;

FIGS. 2 and 3 schematically represent two-dimensional plots of $\log_2$ (MIC) versus light scattering index (LSI) for a particular antibiotic and microorganism at first and second concentrations of the antibiotic respectively;

FIGS. 4a, 4b and 4c represent three-dimensional graphical depictions of MIC as a function of two different concentrations of antibiotic for particular microorganisms;

FIGS. 7 and 8 are tables showing the equations obtained by regression analysis for the presently preferred exemplary embodiment of this invention providing MIC values as a function of growth measurements expressed as the light scattering index (LSI) for different predetermined concentrations of different antibiotic and general classes of microorganisms;

FIG. 9 is another table revealing the limits within which the MIC may be evaluated according to the equations of FIGS. 7 and 8;

FIG. 10 is a table showing the agreement between MIC values obtained with the exemplary embodiment of this invention and accepted reference techniques by four different medical investigators;

FIGS. 11–37 comprise a series of tables having discrete entries of MIC values for predetermined increments of measured growth expressed as a light scattering index for each of two different concentrations of antibiotic. There is a separate table for each combination of antibiotic and general class of microorganisms and the equations corresponding to such combination of antibiotic and microorganism (taken from FIGS. 7 and 8) are also shown in FIGS. 11–37.

Figure 1:
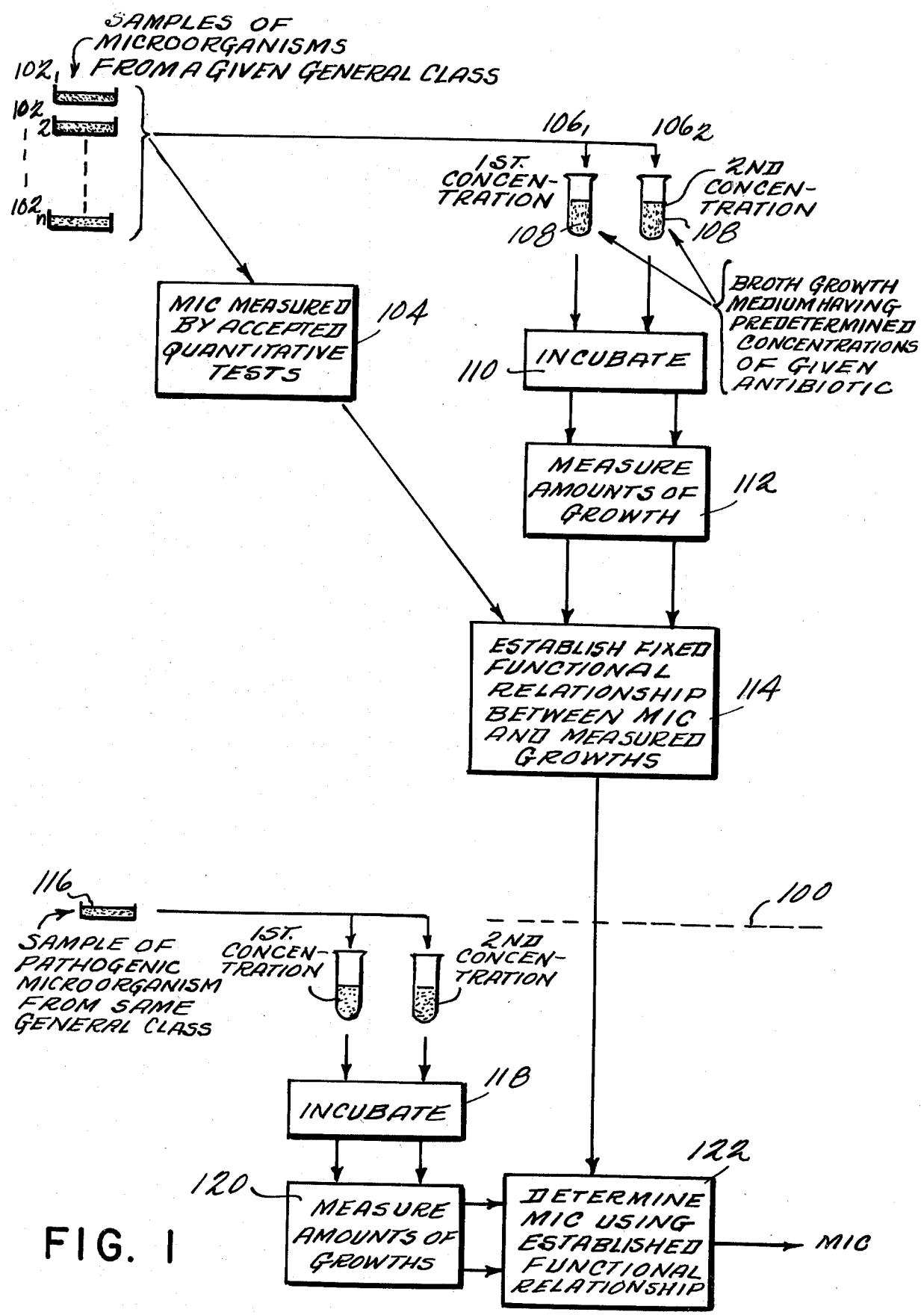

It has been discovered that a fixed functional relationship may be established between the minimum inhibitory concentration (MIC) and the growths of a microorganism from a given general class in the presence of two different concentrations of a given antibiotic. The method steps above dotted line 100 in FIG. 1 are involved with the establishment of this fixed functional relationship and are normally done in advance by a supplier of method and apparatus according to this invention. The method and apparatus is designed to use such a pre-established functional relationship in a normal hospital laboratory environment to rapidly and accurately determine MIC values of given pathogenic microorganisms of interest. The method steps depicted in FIG. 1 below dotted line 100 are then carried out by the hospital laboratory in accordance with this invention.

To start with, a number of samples $102_1$, $102_2$ . . . $102_N$ of microorganisms from a given general class are obtained. For example, different species of bacteria may be obtained from one of the general classes of bacteria comprising: staphylococci, enterococci, enterobacteriaceae, or gram-negative glucose non-fermenters.

If these different species of microorganisms from a given general class are analyzed to determine their MIC for a given antibiotic by accepted quantitative tests, as at 104 in FIG. 1, different MIC values will be established corresponding respectively to the different species of microorganisms involved.

Likewise, if the various species of microorganisms from a given general class are permitted to grow in a broth growth medium having a predetermined concentration of a given antibiotic, different amounts of growth will occur during given incubation times. Prior to saturation limits of "growth" and "no growth" these will be a continuum of growth values which as will be explained, may be used to establish a fixed functional relationship with MIC. Even where relatively rapid growth saturation occurs during the incubation period, data from growth occurring in two or more different antibiotic concentrations can be used to establish the desired functional relationship. If the concentration of antibiotic involved is changed, the amount of growth which occurs during the incubation time will also change.

In FIG. 1, the samples of microorganisms from a given general class are distributed into two separate chambers or containers $106_1$ and $106_2$, each containing a broth growth medium 108. However, the broth growth medium 108 in chamber $106_1$ has a first predetermined concentration of the given antibiotic while chamber $106_2$ has a second and different predetermined concentration of the same antibiotic.

These inoculated growth mediums having different concentrations of antibiotic are then incubated at 110 for a predetermined length of time and/or for a time sufficient to permit a predetermined amount of growth to occur in a control growth medium having no antibiotic present. A fixed time period of suitable duration (e.g., 5 hours) under carefully controlled temperature and other physical conditions to facilitate growth is preferably employed in conjunction with a control growth level measurement. Typically, the incubation step 110 is carried out in a conventional shaker-incubator of the type used in the earlier Pfizer Autobac 1 system described in U.S. Pat. No. 3,832,532. The containers $106_1$, $106_2$ and other similar containers may also conveniently be embodied as the different chambers in the cuvette described in U.S. Pat. No. 3,832,532. Similarly, the amounts of microorganism growth may be measured at 112 using the apparatus described in U.S. Pat. No. 3,832,532 which provides a light scattering index (LSI) having values between 0 and 1 which are inversely related to the amount of microorganism growth normalized with respect to the growth level in a control chamber having no antibiotic content.

Figure 2:
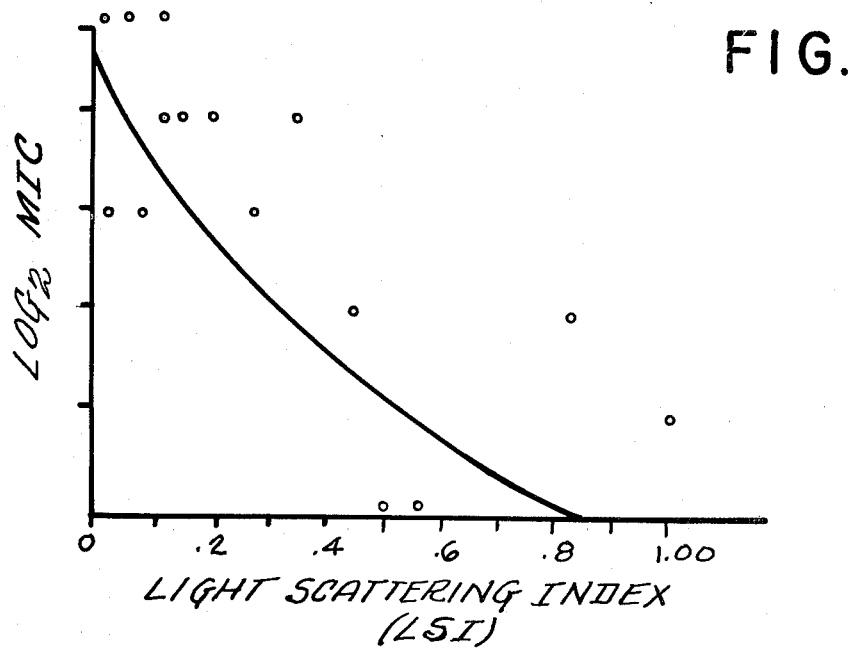
Figure 3:
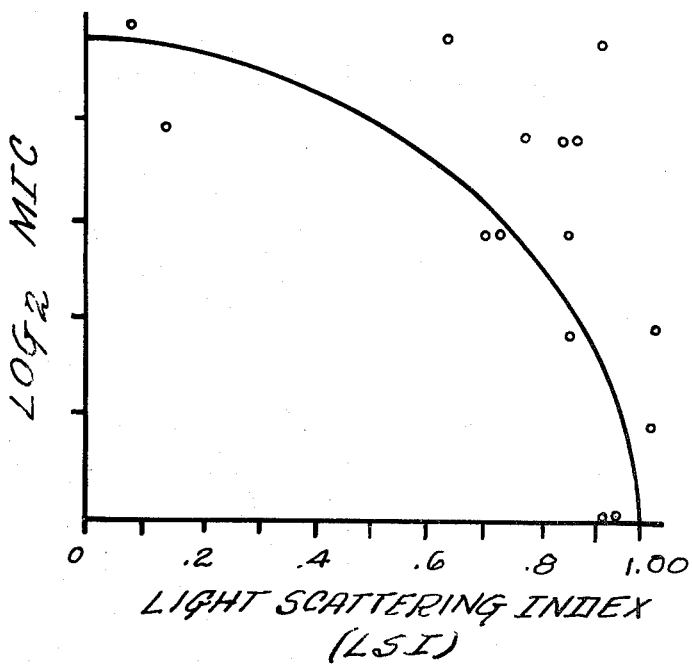

The results of measurements of MIC at 104 and measurement of growth at 112 for two different concentrations of the antibiotic gentamicin and various species of microorganisms taken from the general class staphylococci are shown in FIGS. 2 and 3. The scattered marks in these two-dimensional plots represent data points and the curve which has been drawn in on the graph manually is simply a schematic qualitative showing that the data points seem to follow a logical pattern albeit they are widely scattered about any line or curve which can be drawn in the two-dimensional plane. As will be described subsequently, there are a few combinations of antibiotic and microorganisms for which a well-defined functional relationship may be established in only a two-dimensional plot such as in either FIGS. 2 or 3. However, in general, it has been discovered that individual two-dimensional plots such as FIGS. 2 and 3 do not provide a well-defined functional relationship which could be used for accurately determining MIC from measured LSI values.

On the other hand, the qualitative recognition of a faintly discernible pattern of data points in such two-dimensional plots as FIGS. 2 and 3 has now led to the discovery that if such data is combined and plotted in three dimensions, a rather precisely defined three dimensional surface (as representively shown in FIGS. 4a, 4b and 4c) is defined by the plotted data points. In general, approximately 95% (see FIG. 10) of all data points fall on the surface or so close to the surface as to be well within the precision limits of accepted MIC measurements. Thus, as will be described more fully below, when conventional regression analysis techniques are utilized for precisely determining a mathematical equation describing a three-dimensional surface best fit to the accumulated data (as schematically depicted in FIGS. 4a, 4b and 4c for typical combinations of antibiotic and microorganism), the MIC for any microorganisms from within the same general class may be determined precisely, accurately and rapidly as a function of the measured LSI for two different concentrations of a given antibiotic. It has also been determined that a different functional relationship exists for any given combination of antibiotic and general class of microorganisms.

As will be appreciated by statisticians skilled in the art of regression analysis, there are many conventional regression analysis techniques which may be employed so as to ascertain the exact equations for three-dimensional surfaces such as those shown in FIGS. 4a, 4b and 4c which provide a best fit to the measured data points. Since such conventional regression analysis techniques are already known and are not a part of this invention, no detailed description of such is believed necessary. Such techniques are described for example, in *Applied Regression Analysis* by Draper and Smith, published by John Wiley & Sons, 1966. Additionally, suitable regression analysis techniques are commercially available in ready to use computer programs. For example, program BMDP2R (linear regression analysis) and program BMDP3R (non-linear regression analysis) available from the Health Sciences Computing Facility, University of California at Los Angeles were used in deriving the equations disclosed herein. In any event, specific equations for specific combinations of antibiotic and general classes of microorganisms established for the presently preferred exemplary embodiment of this invention are explicitly detailed in the following description.

Referring back to FIG. 1, once the fixed functional relationship has been established at 114, then, in accordance with this invention, any given sample 116 of pathogenic microorganism taken from the same general class is permitted to grow in a broth growth medium having the same predetermined concentrations of the same given antibiotic as used earlier in establishing the fixed functional relationship between MIC and such measured growth values. Similarly, these inoculated growth medium containers (e.g., the different chambers in a cuvette as described in U.S. Pat. No. 3,832,532) are incubated at 118 under substantially the same conditions as were used earlier at 110. Again, the incubation may be carried out in a conventional and commercially available incubator-shaker as described in U.S. Pat. No. 3,832,532 for a time period required to increase the number of microorganisms in a controlled growth medium chamber having no antibiotic present and/or for some predetermined time interval (e.g., 5 hours). Thereafter, the relative amounts of microorganism growth occurring in the presence of different concentrations of the antibiotic are measured at 120 in a manner substantially identical to that used earlier at 112 so as to obtain corresponding LSI values.

Once the two LSI values are known for a given combination of organism and antibiotic, the MIC may be determined at 122 using the previously established fixed functional relationship. The fixed functional relationship may be in a form of a table having discrete entries for predetermined increments of measured growth or it may be a fixed mathematical functional relationship in the form of an equation which provides an MIC value for the measured LSI growth values. This determination at 122 may be conducted either entirely manually or automatically when the fixed functional relationship (in either tabular or equation form) is accessible to a properly programmed computer.

The apparatus and method described in U.S. Pat. No. 3,832,532 for antibiotics susceptibility testing dispenses antibiotic containing paper discs into the various cuvette chambers where, during the incubation and shaking period, the antibiotic is eluted from the disc to provide a required concentration of antibiotic within the liquid broth growth medium. This same general procedure is preferred in the exemplary embodiment of the present invention. However, since the earlier susceptibility testing system was only concerned with qualitative rather than quantitative results, there was no requirement for the discs to be extremely accurate dispensers of quantitative amounts of antibiotic. Typically, the actual amount of antibiotic substance contained in any given disc may vary by approximately 30% or so in such qualitative systems without seriously impairing the qualitative results.

The antibiotic containing paper disc used in the past for such qualitative measurements were usually made from larger sheets of filter-type paper. These larger sheets of paper were usually soaked in a liquid solution of the antibiotic after which the paper sheets were dried and the antibiotic containing discs were then punched out from the larger sheet of paper. The variations in actual content of antibiotic between individual discs manufactured according to this process is believed to be due, at least in part, (a) to variations and thickness from one part of the filter paper sheet to another, (b) to uneven drying of the paper (again partly due to differences in thickness) wherein earlier dried portions of the paper would receive extra antibiotic through migration of the remaining liquid material (e.g., capillary action), and (c) to the fact that antibiotics of the beta lactam type (e.g. penicillins) are easily hydrolyzed to inactivity thus making the final effective antibiotic concentration a function of drying time and possibly other parameters.

However, for the quantitative MIC determinations contemplated by the present invention, it is generally necessary to have more precisely predetermined concentrations of antibiotic in the cuvette chambers. For example, at least 10% precision of such concentration values is preferred in the present invention.

To achieve such necessary higher precision, the antibiotic containing discs used in this invention are manufactured according to a different technique. In particular, the individual paper discs are punched from a filter-type paper before any antibiotic treatment has occurred. Typically, such discs are on the order of one-fourth inch in diameter and the filter paper is on the order 0.020 inches in thickness. Thereafter, a very accurate dose of antibiotic containing liquid is individually dispensed (e.g., from a Hamilton syringe, micropipette, etc.) onto each individual disc. Using conventional dispensing techniques, it has been able to obtain an accuracy in dosage per paper disc which varies by only approximately 3% within one standard deviation. These individual paper discs are then dried very rapidly (to avoid inactivation of the antibiotic) with hot moving air at a temperature of approximately 140° F. to 160° F. Care must be taken to prevent the hot air from being so hot that it decomposes the active antibiotic substances. For example, the individual discs may be passed through a drying tunnel of approximately 0.083 ft$^2$ cross-section on a moving metal belt such that it takes approximately five minutes to pass through the drying tunnel while approximately 150 CFM of air between 140°–160° F. also passes through the tunnel. The discs are considered to be dry when they contain less than 2% moisture and are thereafter maintained under appropriate temperature and humidity conditions so as to preserve the antibiotic substance according to conventional practices.

In the presently preferred exemplary embodiment, the microorganism growth is measured by obtaining a light scattering index (LSI) as described in U.S. Pat. No. 3,832,532. However, as those in the art will appreciate, there are a great many different accepted techniques for effectively measuring the numerical concentration of microorganisms within a growth medium such as a liquid broth. For example, instead of scattered light as in the preferred embodiment, light absorbance or light transmission may be utilized albeit such procedures may be less sensitive and less stable than the preferred light scattering technique. In addition, one may use coherent or laser sources of light rather than the quartz-halogen source described in U.S. Pat. No. 3,832,532. It is also possible to measure changes in electrical impedance, caloric (heat) output, carbon dioxide evolution, radioactivity, color, Ph, ATP plus luciferin, and other parameters as will be apparent to those in the art.

The liquid broth growth medium used in the preferred embodiment is preferably filtered through a membrane having a mean pore size on the order of 0.22 microns so as to enhance its optical purity. This broth is of the Mueller-Hinton type; however, the normal starch component of a Mueller-Hinton type of broth has been replaced by glucose in the preferred embodiment so as to enhance the optical purity of the resulting broth and to also enhance the rapid growth of certain types of bacteria, particularly, those from the class of enterococci. The exact composition of this broth will be detailed below. However, as those in the art will appreciate, the broth actually used within a given system must be standardized and carefully maintained by quality control tests so as to give reliable and consistent results.

It is also important to note that the incubation time period is preferably shortened from the more usual 16–20 hours for reasons other than mere savings of time. In particular, shortening the incubation period (e.g. to 5 hours or until a certain standard numerical concentration of microorganisms has been established in a control chamber without the presence of any antibiotic) provides a continuum of LSI data value points thus making it possible to establish and recognize the fixed functional relationship between MIC and such a continuum of measured growth values. If the incubation period is permitted to proceed too long, then all the measured growth values will tend to concentrate on either of two extreme levels indicating only "growth" or "no-growth" and thus making it more difficult, if not impossible, to establish well-defined continuous functional relationships that may be used to quickly obtain MIC values in accordance with this invention. With the presently preferred exemplary embodiment, it is believed that approximately 5 hours of incubation time provides the optimum agreement between MIC values obtained with the established functional relationship and those obtained through presently accepted quantitative test procedures. However, the optimum incubation time will no doubt vary with different embodiments of this invention as will be appreciated. Furthermore, even with the exemplary embodiment of this invention, the actual incubation time for any given test is additionally controlled by the number of microorganisms that have grown in a control chamber of the cuvette wherein no antibiotic has been added.

Although the fixed functional relationship between MIC and measured LSI values is based on standard quantitative MIC measurements which have a maximum precision on the order of ±a two-fold dilution, the MIC which is determined from the functional relationship may actually have more precision because of the inherent smoothing and/or interpolation which results from best fitting the functional relationship to a statistically large number of measured data points. Another technique for enhancing the precision of the MIC determined according to this invention would be to use more precise quantitative MIC measurements in the process of establishing the fixed functional relationship between MIC and the measured LSI values. For example, instead of using the standard series of two-fold dilutions, one could use a series of lesser dilution intervals to obtain a more precise quantitative value for the actual MIC corresponding to given LSI measurements used in establishing the fixed functional relationship.

Figure 5:
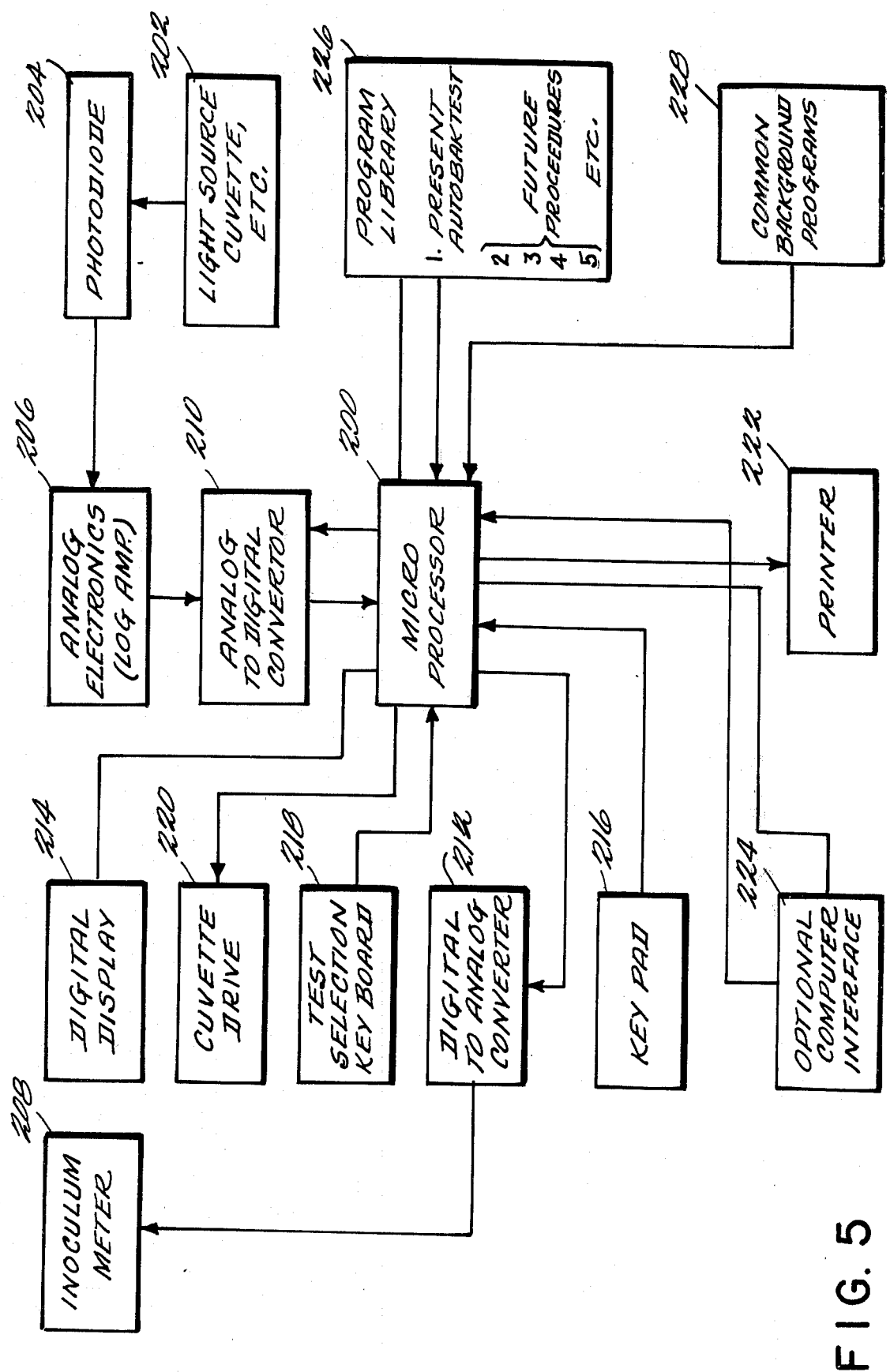
FIG. 5 is a block diagram of suitable apparatus for automatically or semiautomatically performing the process of this invention.
Figure 6:
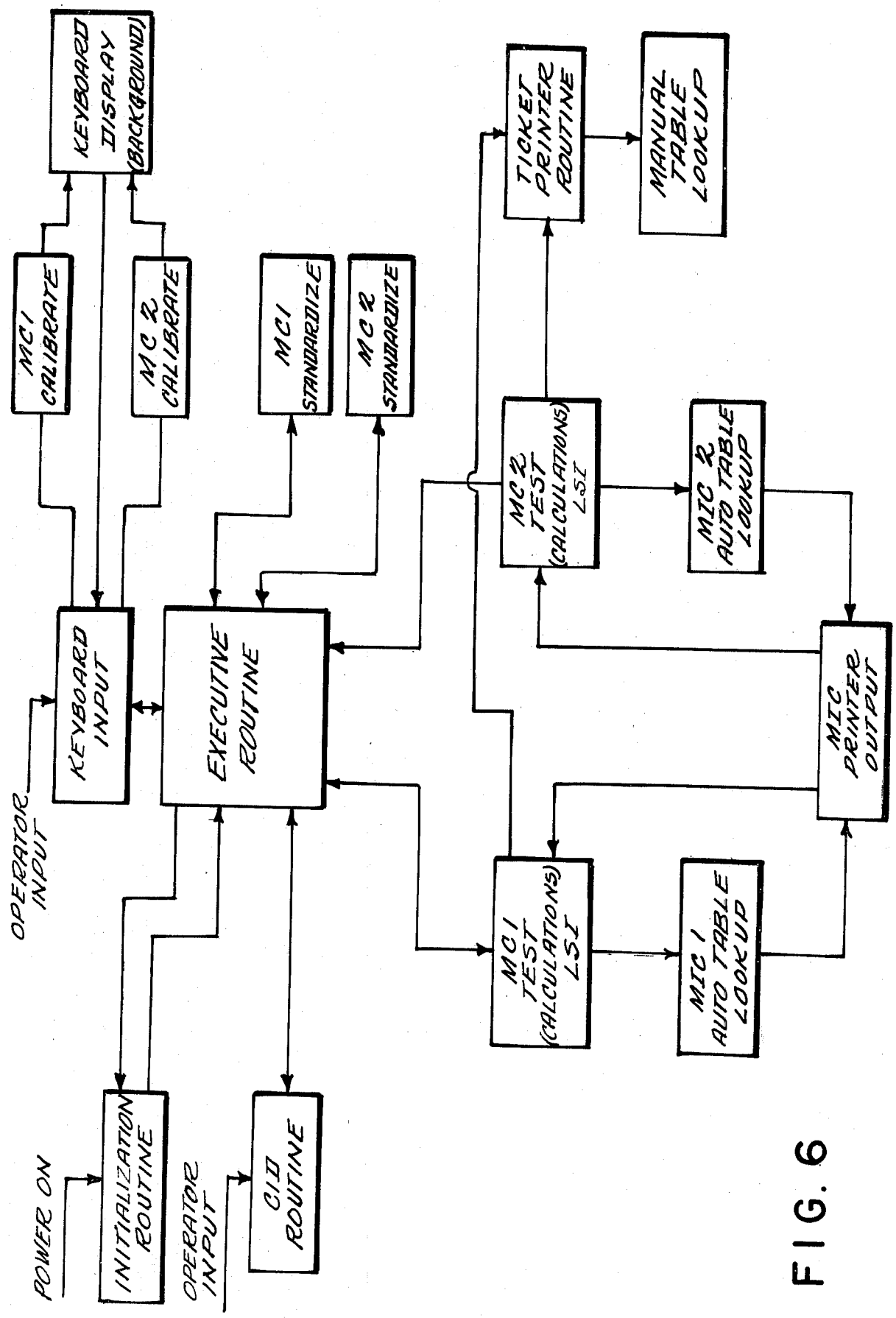
FIG. 6 is a flow diagram of a suitable preferred computer program to be used in the micro-processor of the system shown in FIG. 5.

As mentioned earlier, this invention may be carried out, if desired, using commercially available apparatus as described in U.S. Pat. No. 3,832,532, for standardizing the inoculated growth medium, for containing the growth medium in the presence of predetermined concentrations of antibiotic substances, for incubating and shaking the growth medium container or cuvette and for subsequently measuring the microorganism growth in comparison to that in a control chamber without antibiotic and providing normalized numerical values of a light scattering index (LSI). However, in the presently preferred exemplary embodiment of this invention, the apparatus shown in U.S. Pat. No. 3,832,532 has been modified as indicated in FIGS. 5 and 6. Here, a general purpose programmable microprocessor 200 controls the machine operation. This microprocessor may be, for example, of the type IPC 16/A 500D by National Semiconductor.

The light source, the cuvette, and the related mechanical and electromechanical devices 202 which provide the requisite scattered light to a photo diode 204 are all as described in U.S. Pat. No. 3,832,532. The logarithmic amplifier and other analog electronics circuits 206 are also as previously described in that patent. However, rather than directly driving meter 208, the analog signal is now converted to digital form at 210 (utilizing a conventional dual slope A/D converter with 10 bit accuracy) and provided to microprocessor 200. In turn, microprocessor 200 is capable (through appropriate program control) of driving the meter 208 according to any desired scale factor through a conventional digital-to-analog converter 212 as will be appreciated from FIGS. 5 and 6. The converter 212 may, for example, be of the type AD 7520 LN by Analog Devices.

In addition, the system shown in FIG. 5 incorporates a conventional digital display 214 for communicating visually with an operator and a conventional keyboard 216 by which the operator may communicate information to the microprocessor 200. Another set of special function keys 218 is provided for manipulation by the operator so as to select particular pre-programmed test procedures as will be later explained and/or as may be desired if the system of FIG. 5 is programmed to provide tests in addition to that contemplated by the present invention. Although the mechanical and electromechanical elements of the cuvette drive 220 are as previously described in U.S. Pat. No. 3,832,532, they are now under program control by microprocessor 200 as should also be apparent from FIG. 5. Finally, the system in FIG. 5 includes a conventional printer device 222 so that digital outputs may be provided in printed form. If desired, an optional computer interface 244 may be provided so that the system of FIG. 5 may cooperate with other computing facilities.

The microprocessor 200 is also provided with conventional memory devices 226 and 228 for storing programs, data, etc. as may be necessary or desirable and as is conventional practice. For example, memory device 226 may comprise the INTEL 2716 EPROM Memory having 2,000×8 bits. Up to eight of these units may be conventionally used and approximately three will be needed for the system shown in FIG. 5. Additional program material may be stored in memory 228 which may comprise, for example, a type MM 5204Q EPROM Memory available from National Semiconductor and having 512×8 bits in each of 12 such units.

Suitable programs for driving microprocessor 200 are believed to be readily designed by those ordinarily skilled in the art once the basic method used by this invention is understood and in light of the following discussion. Accordingly, no detailed description of a particular program listing is believed necessary. Nevertheless, a general description in flow diagram form of the program employed in the system of FIG. 5 is shown in FIG. 6. This program will be described in more detail later.

The presently preferred embodiment of this invention provides an automated objective method for the determination of the minimum inhibitory concentration (MIC) of antibiotic required to inhibit the growth of pathogenic organisms. The methodology involved offers at least the following advantages:

(a) High agreement with a microtube version of the ICS (International Collaborative Study) Broth Dilution Methodology as described by Ericsson et al (ca. 95% average with a range of 92% to 98% agreement within ±one two-fold dilution for the various antibiotics).

(b) Significantly less variability (vis-a-vis both intra and inter laboratory performance) than that obtained with a microtube version of the ICS Broth Dilution Methodology.

(c) Rapid results (e.g., five hour incubation time).

(d) Results obtained using only two antibiotic concentrations which are conveniently available on paper disks—no dilutions to prepare.

(e) A highly standardized procedure which reduces the possibility of human error.

The basic limitation of the exemplary embodiment using broth is that, as with any broth method, it is not possible to known with absolute certainty whether or not a pure culture has been tested without simultaneously streaking a plate for subsequent examination. The use of this method is, of course, also restricted to particular drug/organism combinations for which an appropriate fixed functional relationship exists between MIC and measured LSI values.

As presently embodied, the system comprises a disposable plastic cuvette, instrumentation, and several reagents which are described below:

(a) The Cuvette

This multichambered plastic device is substantially identical to the cuvette described in U.S. Pat. Nos. 3,832,532 and 3,895,661. It is formed by optically clear polystyrene and provides 12 test chambers which receive test antibiotics in the form of elution disks and one control chamber which receives no antibiotic. Broth, containing a standardized inoculum, is introduced into the cuvette reservoir and is distributed by simple manipulation into the control chamber and the 12 test chambers. The cuvette is then incubated for five hours in an Autobac incubator shaker (also described in U.S. Pat. No. 3,832,532). At the end of the incubation period, the cuvette is transferred to the photometer (see below) and the growth in the cuvette chambers is optically evaluated.

(b) The Photometer

The photometer is similar to the Autobac 1 photometer described in U.S. Pat. No. 3,832,532 and which is already in commercial distribution. Preferably the photometer is made to permit both MIC testing and the earlier marketed susceptibility (AIS) testing. The photometer performs the following functions:

i. Standardization of Starting Inoculum:

The number of organisms required for the starting inoculum is determined by inserting an inoculum standardization tube into the photometer and reading the meter 208. The photometer can be programmed to give either $10^7$ (MIC 2 mode) or $10^8$ (MIC 1 mode) Colony Forming Units (CFU)/ml of inoculated saline as required in the testing protocol.

ii. Evaluation of Antibiotic Effect:

After incubation, the cuvette is inserted in the photometer and the growth in each chamber is determined optically and compared with growth in the control chamber. This is accomplished by calculating a Light Scattering Index (LSI) which is a normalized ratio of the logarithm ($\log_{10}$) of the growth in the test chamber to the logarithm of the growth in the control chamber. This value, which ranges from 0.0 for no inhibition of growth to 1.0 for complete growth inhibition, is used to calculate results in both the earlier susceptibility and the new MIC test methodologies.

A beam of light traverses the inoculum in the cuvette chamber. The amount of light scattered in the forward direction (e.g., at an angle of 35°), is directly proportional to the organism population and is measured by a photocell and associated electronic circuitry. From these measurements LSI values are calculated for each test chamber. In susceptibility testing these LSI values are directly interpretable as resistant (R), intermediate (I) or susceptible (S). Each LSI value is printed on a suitable reporting ticket together with the associated interpretation (R, I, or S). In MIC testing a more sophisticated protocol is required for the calculation of MIC values from pairs of LSI readings. MIC values are determined from the LSI manually by use of tables or equations or automatically by use of an optional preprogrammed computer.

(c) The computer system

As already explained, the computer system comprises keyboards 216; 218, digital display 214 and an alphanumeric auxiliary printer 222. These items, when connected to the photometer, allow the user to enter, via the keyboard, the identity of a particular panel of antibiotics being tested in the photometer and to utilize the photometer microprocessor to directly compute for each test organism the MIC values of the antibiotics in the panel being used.

(d) The incubator

The Autobac 1 Incubator/Shaker as described in U.S. Pat. No. 3,832,532 is already commercially available. It has a capacity of 30 cuvettes and is designed to maintain a temperature of 36° C. while rotating the cuvettes at 220 rpm in a ¾" circle.

(e) The disk dispenser

The Autobac 1 Disk Dispenser as described in U.S. Pat. Nos. 3,832,532 and 3,899,011 is also already commercially available. It is designed to simultaneously dispense up to 12 antibiotic elution disks into the cuvette test chambers.

(f) Broth

The Broth is a Mueller-Hinton like broth developed especially for MIC testing in this system. The broth is preferably packaged in glass tubes designed to attach to the cuvette. Each tube contains 18 ml of sterile, optically clear broth. The presently preferred broth (pH ca. 7.3) has the following approximate composition in grams per liter: Acid Hydrolyzate of Casein=17.5, Brain Heart Infusion=4.0, Dextrose=2.0, Total Calcium=0.06 and Total Magnesium=0.03.

Depending on the drug/organism combination, two starting broth inoculum concentrations are used in the cuvette: (1) for gram negative organisms being tested with beta-lactam antibiotics (ampicillin, carbenicillin, cephalothin and penicillin G) an inoculum level of about $10^6$ Colony Forming Units (CFU)/ml of broth is used; and (2) for all other combinations, an inoculum level of about $10^7$ CFU/ml of broth is used.

(g) Inoculum Standardization Solution

The Inoculum Standardization Solution is already commercially available as part of the Autobac susceptibility testing system. It is supplied in one liter bottles and is a sterile, optically clear phosphate-buffered saline solution (pH=7.0) used to prepare standardized suspensions of organisms by optical comparisons therewith. It has the following approximate composition per liter of distilled water: sodium chloride, 4.2 grams; potassium phosphate, dibasic, 3.2 grams; and potassium phosphate, monobasic, 1.6 grams.

(h) Inoculum Standardization Tubes

Inoculum Standardization Tubes are also commercially available as part of the Autobac susceptibility testing system, and are 16 mm×125 mm optically screened, glass tubes used in the photometer to prepare standarized suspensions of organisms.

(i) Antimicrobial Test Disk (Elution)

This MIC testing system employs two precision elution disks of each antibiotic at concentrations carefully selected to span the useful therapeutic range of the antibiotic and to closely correlate the resulting MIC values with classical methodology.

The MIC test methodology evolved from the Autobac susceptibility test methodology. In the susceptibility test methodology, a suspension of organisms is challenged with a concentration of antimicrobic in a test chamber of the cuvette and compared to the result obtained in the control chamber to which no antimicrobic has been added. The effectiveness of the antimicrobic agent in inhibiting the growth of the organism is rated on a scale of 0.0 to 1.0 derived by comparing growth in the test chamber to growth in the control chamber.

The MIC test methodology evolved from the Autobac susceptibility test methodology. In the susceptibility test methodology, a suspension of organisms is challenged with a concentration of antimicrobic in a test chamber of the cuvette and compared to the result obtained in the control chamber to which no antimicrobic has been added. The effectiveness of the antimicrobic agent in inhibiting the growth of the organism is rated on a scale of 0.0 to 1.0 derived by comparing growth in the test chamber to growth in the control chamber. This antimicrobic inhibition index is termed the LSI where a reading of 0.0 means no inhibition and 1.0 means complete inhibition of growth. In the susceptibility test procedure, disk masses are chosen so that LSI values can be converted directly into resistant, intermediate and susceptible results as follows:

| Interpretation | LSI Range (Except Penicillin G) |
|---|---|
| Resistant | 0.00–0.50 |
| Intermediate | 0.51–0.59 |
| Susceptible | 0.60–1.00 |

For penicillin G the resistant range is 0.00 to 0.90 and the susceptible range is 0.91 to 1.00. In most cases, determination of MIC values from a single concentration of antibiotic is not possible over any meaningful span of MIC values since the LSI value will change (even in a 5 hour period) from 0 to 1 in as little as a concentration range of two-fold dilution. That is if one has available only data from one measurement where such a sharp change in LSI occurs, one can, at most, only infer that the MIC is above or below the concentration employed. However, with data from plural concentrations, the probability that all data will be at saturation levels (i.e., LSI subtantially zero or one) is significantly reduced. For this reason it was decided initially to employ three disk masses for each antibiotic and to separate these by two or four two-fold dilutions as required around the region of therapeutic interest. The antibiotics and the disk masses chosen are listed in TABLE 1:

TABLE I

| Antibiotic | Antibiotic Disk Masses[1] Nominal Disk Masses |
|---|---|
| Ampicillin | 3*, 12, 48* mcg |
| Carbenicillin | 12*, 48, 192* mcg |
| Cephalothin | 3*, 12, 48* mcg |
| Chloramphenicol | 12*, 24, 48* mcg |
| Clindamycin | 1.5*, 3, 6* mcg |
| Gentamicin | 3*, 6, 12* mcg |
| Kanamycin | 6*, 12, 24* mcg |
| Methicillin | 3*, 6, 12* mcg |
| Penicillin G[2] | 0.188*, 3, 48* IU |
| Penicillin G[3] | 3, 12*, 48* IU |
| Tetracycline | 3*, 6, 12* mcg |

[1]Note that the antibiotic is eluted into approximately 1.5 broth so that the actual broth concentrations are ⅔ of the amounts given in the above table.
[2]Staphylococci only.
[3]Organisms other than Staphylococci.
*These are also the two disk masses used for the later discovered techniques of this invention. The preferred resulting pair of antibiotic concentrations, in general, span a four to sixteen fold dilution range centered about the useful therapeutic range of that antibiotic.

These disk masses were employed in adjacent chambers of a cuvette and the LSI's obtained were used to evaluate the degree of growth inhibition with each concentration of antibiotic. Each test concentration of antibiotic could be judged as inhibitory or non-inhibitory to the specific organism under test by experimentally establishing a thresh-hold or "breakpoint" LSI value below which the antibiotic was judged non-inhibitory and above which the antibiotic was judged inhibitory. The MIC was then obtained by comparing the test LSI measured by the photometer in the presence of each antibiotic concentration to the breakpoint LSI as shown in the example given in TABLE 2 for tetracycline for which a 0.70 LSI breakpoint was used:

TABLE 2

For Tetracycline/Staphylococci:
Initial Inoculum = $10^7$ CFU/ml
Incubation = 5 hrs., 36° C., 220 rpm

| | Disk 1 (3 mcg) | Disk 2 (6 mcg) | Disk 3 (12 mcg) | |
|---|---|---|---|---|
| IF LSI's ARE | ≧0.70 | ≧0.70 | ≧0.70 | mic ≦ 2 mcg/ml |
| IF LSI's ARE | * | ≧0.70 | ≧0.70 | MIC = 4 mcg/ml |
| IF LSI's ARE | * | * | ≧0.70 | MIC = 8 mcg/ml |
| IF LSI's ARE | * | * | * | MIC > 8 mcg/ml |

* = LSI < 0.70

However, it has now been discovered that a new and improved technique is possible for deriving an MIC value from multiple concentrations of antibiotic. Using regression analysis, equations are fitted to the data base collected by challenging large numbers of organisms with various concentrations of an antibiotic. These equations are capable of utilizing the interactive LSI information from two or more antibiotic concentrations simultaneously and, therefore, have an inherent advantage over a simple breakpoint method in which the LSI from any one antibiotic concentration is treated independently from the LSI obtained for any other antibiotic concentration. The regression equations used in the presently preferred exemplary embodiment for converting the LSI values to MIC values are given in FIGS. 7–8 for 27 antibiotic/organism pairs. It will be noted that, in general, the LSI values of only the low and high disk masses (see asterisks in Table I) are necessary to compute the MIC. The actual computation of the MIC is simplified by the use of either a look-up table (examples of which are shown in FIGS. 11–37) or by the use of a computer previously described.

This regression equation methodology also generally allows the MIC to be estimated to $\pm\frac{1}{2}$ two-fold dilution interval and to be extrapolated somewhat above and below the actual antibiotic concentrations used in the test. For example, with 3 and 12 mcg tetracycline disk (yielding 2 and 8 mcg/ml concentrations in the test cell of the cuvette), the MIC range of the method is approximately 1 to 16 mcg/ml in $\frac{1}{2}$ two-fold dilution steps between these limits.

The individual devices comprising the system of FIG. 5 are conventional commercially available items or are straight forward adaptations of the apparatus shown in U.S. Pat. No. 3,832,532. However, the particular combination of components shown in FIG. 5 together with the program depicted in FIG. 6 provide a novel apparatus which greatly facilitates the determination of MIC values by the method of this invention. This apparatus will now be described in greater detail by providing brief primarily functional descriptions. Since the individual apparatus elements are already available to those interested in this art, such brief description should be ample to permit those skilled in the art to make and use such apparatus.

A cuvette reading cycle, which consists of evaluating and recording the organism growth in each cuvette chamber, is activated by inserting a suitable reporting ticket into a printer slot at the front of the photometer. When completely inserted, the test cycle will be initiated and the results will be printed on the ticket.

When activated by the STAND button (keyboard 218), this meter indicates whether or not the concentration of the Inoculum Standardization Solution (the Inoculum Standardization Tube having been earlier inserted into a suitable measurement part) is correct. A center blue region span represents the correct organism concentration for the selected test. A deflection to the right of this blue region (in the OVER region) is an indication that the sample must be diluted in order to achieve standardization and a deflection to the left (in the UNDER region) is an indication that more microorganisms must be suspended in the sample to achieve standardization. Depressing the STAND button places the photometer in a Standardization Mode of operation only if the machine is in proper mechanical status and the proper test mode has been selected. Altering the machine from a proper mechanical status while it is in the Standardization Mode will return to a Stand-by condition.

Depressing a RESET pushbutton (keyboard 218) terminates any operation or cancels the Standardization Mode and puts the photometer in a Stand-by condition. The various machine modes may be visually shown by conventional indicator or status lights as will be appreciated. For example, a READY indicator may turn from red to green when all conditions are satisfied for reading a cuvette. Only when this indicator is green will insertion of a reporting ticket into the printer initiate the test.

Since the machine may later be used for certain tests with non-aerobic microorganisms, an AEROBIC Key (keyboard 218) may also be provided for use when testing aerobic organisms. If so, this key must be depressed for all aerobic tests and calibrate mode operations.

Also, MIC 1 and MIC 2 keys (keyboard 218) select one of two inoculum concentrations (e.g. scale display factors) used for the minimum inhibitory concentration test and its corresponding calibrate and manual mode operations. A TEST key is provided to initiate all normal testing operations (e.g. test programs) while a CAL key initiates all calibration mode operations (background constant and calibration wedge).

The RECALL key will cause the last valid background constant value to be displayed on digital display 214. While the cuvette drive 220 is normally automatically activated under testing program control, a MANUAL key may be used to transfer operation from an automated 13 step sequence system control to a one step-by-step sequence initiated via the PROCEED switch. Each activation of PROCEED advances the cuvette carriage one step at a time and may be used, for example, to check each cuvette well via the digital display 214 for possible optical defects.

An ENTER key may be used to enter an average value of observed light scatter into the photometer memory when manually setting the background constant.

A REMOTE key may be provided to activate peripheral equipment, such as an optional MIC computer. The digital display 214 may comprise an L.E.D. (Light Emitting Diode) readout used to display the backgrond constant, or, Light Scattering Indices. The key pad 216 may be used by the operator for manual entry of data into the photometer.

The proper sequential selection of the switches on keyboard 218 will select any one of several photometer modes. For each determination that the photometer performs, (either AIS or MIC $\frac{1}{2}$), one of three operational modes may be selected:

1. The Standardization Mode is used to test the initial saline inoculum levels of the selected isolate and has already been described.
2. In the Calibration Mode the actual logarithm of the light scattering voltage (LSV) of each chamber (including the control chamber) as measured by the photometer is printed. This allows the photometer to be used for research work and allows the user to determine the background scatterings of cuvettes and broth. In Calibrate Mode, no interpretation is printed.
3. In the Test Mode the photometer first computes the Growth Index (GI) for cuvette control chamber 0 and then computes the Light Scattering Index (LSI) for chambers 1 to 12. For AIS Testing, the LSI values are used directly to determine the Resistant (R), Intermediate (I), or Susceptible (S) interpretation. For MIC Testing, the LSI values for the two antimicrobic disks are used to calculate minimum inhibitory concentration (MIC) using an appropriate equation or table.

During the photometric measurement, light emitted by a 20 watt quartz-halogen lamp is focused and directed by a lens system to the optical area of the cuvette. The cuvette is then advanced through the light beam in discrete steps when a ticket is placed into the printer. The light scattered at an approximately 35° angle to the incident beam is received and measured by the photodetector. The photodetector produces a current output directly proportional to the intensity of light reaching it. Over wide limits, this value is also directly proportional to the number of microorganisms per unit volume and may be used as a sensitive measure of changes in such microorganism concentration. The output of the photodetector is then converted to its logarithmic value and processed by a digital computer 200.

In the Test Mode of operation, computer 200 calculates the Growth Index (GI) for the control chamber and the Light Scattering Index (LSI) for each test chamber and prints this result. In the Calibrate Mode the computer converts the logarithmic voltage to a digital value and prints this result. In addition, the photometer is also used for the standardization of the inoculum as earlier described.

The photometer compares the bacterial concentration in the control chamber of the cuvette (no antimicrobic) with the bacterial concentration in each of the 12 test chambers containing an antimicrobial disk. The comparison is quantified utilizing the following measured parameters.

$G_c$ = The logarithm of the light-scatter intensity or growth in the uninhibited or control chamber at the end of the incubation period.

$G_x$ = The logarithm of the light-scatter intensity or growth in any test chambers at the end of the incubation period.

$G_k$ = The logarithm of the light-scatter intensity prior to incubation. This value is termed the background constant. $G_k$ is determined for each lot of Cuvettes and Broth and entered as a constant in the calculation.

The above quantities are utilized to calculate the following parameters in the Test Mode:
1. The Growth Index (GI) = $G_c - G_k$. This is the logarithmic ratio of the light scattered in the control chamber after incubation to the light scattered before incubation. The Growth Index (GI) is, therefore, equal to the log of the growth multiplication of the organism under optimum growth conditions. The Growth Index is printed on the reporting ticket as the first value.
2. The Light Scattering Index (LSI). If the growth index is equal to or greater than 0.90, the LSI value is determined for each antimicrobic. The first part of the procedure for calculating the LSI value is to calculate the value analogous to the Growth Index for each chamber containing an antimicrobic or $G_c - G_x$. This value can vary in three hours over a two decade range, depending on the rate of organism growth. It is, therefore, not suitable as a numerical rating of susceptibility. If, however, this value is divided by the Growth Index for the control chamber, ($G_c - G_k$), a growth normalized value is obtained which is defined as LSI or, $$LSI = \frac{G_c - G_x}{G_c - G_k}$$

This is an index of growth which has a range of 0.00 to 1.00 with 0.00 representing complete resistance and 1.00 complete inhibition. This scale of 0.00 to 1.00 can also be considered a percent inhibition index.

The photometer is automatically programmed to reject a cuvette if the Growth Index is less than 0.90 (i.e., the antilog$_{10}$ of 0.9 equals 8 or approximately three doublings of the bacterial population) since it has been found that the data can be unreliable unless this criterion is met. If in the specified test time sufficient growth has not been achieved due to slow growing organisms, the cuvette may be returned to the Incubator/Shaker for an additional incubation period. The Growth Index is printed on the reporting ticket as the first value. If the Growth Index is less than 0.90, no subsequent data are printed and the test is terminated.

Automated MIC computation may be provided when the photometer is properly programmed. Information comprising a sample accession number, the drug panel identification and the clinical isolate identification may be entered by an operator as follows and observed on the digital display 214;
1. Accession Number—A sample identification number consisting of up to nine digits.
2. Isolate Number—A one digit number used to identify a specific isolate.
3. Drug Panel Number—Used to select one of six possible MIC drug panels desired.

An MIC report may include the following information:
1. Accession Number, up to nine digits.
2. Isolate Number, one digit.
3. Drug Panel Number, two digits.
4. Test Chamber Number (1-12).
5. The Growth Index, which must be 0.90 or greater or the photometer will stop its test at that point.
6. Six pairs of LSI values, each rounded off to the nearest tenth.
7. The corresponding MIC value for each pair given in MCG/ml or IU/ml for Penicillin G.
8. The corresponding drug for each of the six MIC values.

Calibration for particular lots of broth and cuvettes may be carried out by selecting the AEROBIC MIC 1 (or MIC 2) CAL functions. Once a reporting ticket has been inserted in the printer, the photometer will print the LSV values for the 13 chambers and the average value will appear on the numerical display. If an out of tolerance deviation in chamber LSV is detected for more than two chambers, an error message (e.g., consisting of three backward C's) will appear on the display. If this occurs, an additional cuvette should be prepared. When an acceptable cuvette has been run, a number between 2.40 and 3.20 will appear on the digital display 214. Then, the second cuvette should be run in the same way. If it is also acceptable, the value on the digital display 214 will indicate the average chamber LSV for all the chambers in the two cuvettes. If the second cuvette is defective, the display will flash and it will be necessary to run yet another additional cuvette.

Once two acceptable cuvettes have been run, a stable number will appear on the digital display. If this is between 2.40 and 3.20 the cuvettes and broth are acceptable. This number is then entered into the photometer memory by pressing CAL and ENTER on the control panel simultaneously. To confirm that the number has been entered, RECALL may be pressed and the entered number will reappear on the display. Calibration for the MIC 2 mode is similarly achieved except that here an acceptable result should fall into a range between 2.90 and 3.70.

Once the calibration has been accomplished and the background constants entered (for MIC 1 and MIC 2) for the given cuvette and broth, the photometer is now placed in TEST mode. The two LSI's generated from an MIC test are inserted into the appropriate formula in FIGS. 7-8 and the result is calculated. Note that there is a separate equation for each of the combinations of antibiotic and organism class given. The labor of calculating the result may be eliminated by the use of tables in FIGS. 11-37 which tabulate the result for 0.1 increments of the two LSI values. Any result in which the LSI of the low mass disk exceeds the LSI of the high mass disk by more than 0.2 should be considered erroneous and the test repeated.

Alternately, under control of the program shown in FIG. 6, the photometer itself will analyze and automatically print the MIC results in micrograms/ml (or in international units/ml for penicillin G) avoiding all manual calculations or look-up tables.

The software depicted in FIG. 6 resides in 5 K addresses of 16 bit memory words. The routines residing there are complete and self-contained and allow MIC tests to be selected and run under software control:

INITIALIZATION ROUTINE

When power is applied, this routine initializes both the hardware and software. All lamps and displays are cleared as well as peripheral devices. INITIALIZATION may be entered any time by pressing the RESET button as well as turning the power on. Upon completion, INITIALIZATION exits into the EXECUTIVE routine.

EXECUTIVE ROUTINE

The function of the EXECUTIVE routine is primarily to monitor and control operations and to determine when conditions are correct for running the selected MIC 1 or MIC 2 TEST. The flow through the EXECUTIVE is detailed as follows:

1. The cuvette drive carriage is brought "home" (if not home already).
2. The type of test to be run is selected by the operator using the function selection keyboard, i.e., MIC 1 or MIC 2. The software recognizes the particular keys pressed and responds accordingly by lighting these keys through the KEYBOARD routine.
3. The presence of a cuvette and the photometer access door being closed are monitored by the computer which responds by lighting front panel lights. Furthermore, a "READY" light will become green when both these two conditions are met and an MIC test has been selected. If appropriate, patient data information is also entered and the photometer will automatically begin running the MIC test selected.

CUVETTE INFORMATION DEVICE (CID) ROUTINE

The software control of the CID patient data entry is performed by the CID routine. When the operator presses any numered CID keys (e.g. keyboard 216), the CID routine is temporarily entered in order to service these keys. By this method, the Accession and Isolate numbers (not necessary for MIC determination) pertaining to the patient as well as the antibiotic PANEL number identifying the contents of the cuvette are entered into the computer's memory for later print out with the results of corresponding MIC calculations.

MIC 1 AND MIC 2 TEST ROUTINES

Either MIC 1 or MIC 2 tests may be selected by the operator using the keyboard 218 and entered when the EXECUTIVE routine has determined that physical conditions are correct for the run. Upon entry, the selected routine performs LSI calculations for each chamber based on the following formula:

$$LSI_N = [LSV_N \text{ minus } LSV_O]/[HWC \text{ minus } LSV_O].$$

Where:
$LSI_N$ = Light Scattering Index for the nth chamber.
$LSV_N$ = Light Scattering Voltage from the logarithmic amplifier inputted through the 10-bit A/D converter 210 for the nth chamber.
$LSV_O$ = Light Scattering voltage for the control chamber.
HWC = Background constant for the TEST selected (described in CALIBRATION routines).

The LSIs calculated for each chamber are stored in memory and are used for either of the following two methods for obtaining MICs:

1. Manual Table Lookup

The LSI's are calculated during the MIC 1 or MIC 2 test routines under control of the TICKET PRINTER routine. Knowing these LSI values and the particular combinations of antibiotic and general class of microorganism (grouped in chamber pairs) enables the operator to look up the MICs for the cuvette in the provided MIC TABLES.

2. MIC 1 and MIC 2 AUTO TABLE LOOKUP ROUTINE

This software routine automatically looks up the MIC values for the cuvette. Using the LSI's calculated during the MIC 1 or 2 test routine and the PANEL number entered by CID, this AUTO TABLE LOOKUP routine generates MICs for either the MIC 1 or MIC 2 tests. This is accomplished as follows:

a. The PANEL number previously entered by CID is read from memory by the computer. This number defines the combination of antibiotic/microorganism for each chamber pair in the cuvette. Since each such combination has its own table stored in memory, the PANEL number also identifies the corresponding table for each chamber pair.

b. After identifying the table for a chamber pair, the corresponding LSI values are used to obtain the specific MIC. This is accomplished by each possible LSI combination having a corresponding location in the table in memory. Contained in each of these locations is all the information for the MIC. If the LSI combination is biologically unrealizable, this also will be contained as information. Thus, the computer reading the content of the location in the table for the LSI pair provides the appropriate MIC information.

c. These MIC data are next printed with appropriate units and chamber numbers as well as the antibiotic in each chamber pair. As a reference, the CID PANEL and patient identification numbers are also printed fully under software control. After this printout for the entire cuvette, the software re-enters the EXECUTIVE routine for further operator instructions and another cuvette run.

MIC 1 and MIC 2 STANDARDIZE ROUTINES

MIC 1 and MIC 2 STANDARDIZE routines are entered from the EXECUTIVE routine by operator selection. Light Scattering Voltage from the logarithmic amplifier 206 is inputted as a digital word into the software using the A/D converter 210. Next, the routine changes the digitized voltage by the appropriate scale factor for the MIC type selected. This scales the value to be in range for the front panel meter. Finally, the D/A converter outputs the value to the meter 208 and display 214. Hence, the various meter positions indicate to the operator the level of Light Scatter Voltage or correct inoculum level.

MIC 1 AND MIC 2 CALIBRATION ROUTINES

For both the MIC 1 and MIC 2 TEST calculations, an exclusive HWC (background constant) is required as explained above. This is accomplished before these TEST routines are performed using their respective MIC 1 and MIC 2 CALIBRATION routines. Upon operator selection, using the keyboard, the particular CALIBRATION routine is entered from the EXECUTIVE. Cuvettes are run containing the standard microorganism concentration (different for MIC 1 and MIC 2), under "no growth" condition. A cumulative average LSV value from two or more cuvettes is computed by the CALIBRATION routine and displayed for the operator. Through the keyboard, the operator next enters this displayed value into the memory as the HWC for the associated TEST routine.

TEST PROCEDURE

The following is an abbreviated possible test procedure:

(1) Dispense antibiotic disk sets of choice into the cuvette (up to six pairs of disks may be run in a single cuvette).

(2) Transfer approximately 6 ml of Inoculum Standardization Solution into the Inoculum Standardization Tube.

(3) Transfer morphologically identical colonies from a fresh culture plate to the Inoculum Standardization Tube and vortex mix until a uniform suspension is obtained.

(4) Place the Inoculum Standardization Tube into the Inoculum Standardization Port of the photometer. Depress the AEROBIC, MIC 1 or MIC 2 test selection keys 218 as appropriate which will cause microprocessor 200 to choose the correct scale factor to use in displaying the photodiode signal. With the photometer in the MIC 1 mode, an inoculum level of $10^8$ CFU/ml saline (corresponding to $10^7$ CFU/ml broth) is obtained at a predetermined meter reading and is used for all testing except gram negative organisms being tested with beta-lactam antibiotics. For the latter, the photometer is placed in the MIC 2 mode and will give an inoculum level of $10^7$ CFU ml/saline (corresponding to $10^6$ CFU/ml broth) for a similar predetermined meter reading.

(5) Depress the Standardization key on the control console (to cause microprocessor 200 to choose the correct operating program) and observe the deflection of meter 208. If the meter needle indicates a predetermined standardized number of CFU/ml, the inoculum is of the correct concentration. If over-or-under inoculation is indicated, the appropriate steps are taken by the operator to adjust the concentration of organisms within the inoculum tube.

(6) Using a pipette, transfer 2.0 ml of standardized inoculum into the 18 ml of MIC Broth in the broth tube, cap and mix by gently inverting several times. Note that this procedure results in a ten-fold dilution of the original saline inoculum.

(7) Dispense the broth inoculum into the cuvette and distribute into the cuvette chambers by rotating the cuvette conventionally. The antibiotic-containing disks have preferably already been distributed into all cuvette chambers except for the control chamber.

(8) Place the cuvette on a carrier tray and lock the tray into the Incubator/Shaker.

(9) Incubate for five hours.

(10) Remove the carrier tray from the Incubator/Shaker and remove the cuvette. Place the cuvette in the photometer.

(11) Activate the appropriate AEROBIC, MIC 1 or MIC 2 and TEST selection keys 218 and insert a reporting form into the printer 222 to initiate the analysis and the printing of results by the photometer. Unless a minimum population increase of three generations (i.e. three doublings) has occurred in the control chamber, the test is aborted and incubation is continued until this growth requirement has been met.

(12) If the automatic MIC computation option is used, the MIC results will be printed out on a remote printer (not shown in FIG. 5) directly in the appropriate MIC units. If this option is not used, the LSI values are printed by the ticket printer 222 in the photometer. These LSI values then are converted to MIC using the conversion tables (FIGS. 11-37) and entered on the reporting form manually.

Before cuvettes are read in the photometer, it is necessary to determine and store a background constant value into the photometer memory elements for later use in the calculation of LSI values. This procedure should be done at installation of the instrument and whenever changes in cuvette or broth lots occur. The background constant represents scattered light which passes through the cuvette chambers for a standardized concentration (according to the standardization procedure outlined above) of inoculum-broth mixture. Readings are taken for a number of chambers (e.g., 26) and averaged to obtain the $G_k$ value to be used for the cuvette and/or broth lot then available.

In the preferred embodiment, the cuvettes must be incubated for a minimum for five hours before reading in the photometer. If after five hours the growth index (in the control chamber) is not at least 0.9, the test should be aborted. In such a case the cuvette may be returned to the incubator/shaker for an additional hour's incubation time. If the growth index remains below 0.9, the inoculum is probably defective and the whole test should be redone. A reading should be taken as soon as possible after the required incubation period has been met because prolonged incubation with some antimicrobic/species combinations may cause a shift in MIC value. Furthermore, in the case of very slow growing organisms, prolonged incubation can cause erroneous results due to interference from rapidly growing organisms introduced as trace contaminants in the inoculum.

Since the exemplary system employs a broth method, it is not possible to ascertain when readings are being taken on a mixed culture. Furthermore, since susceptibility testing of mixed cultures can be an unreliable guide to antimicrobial therapy, and since, even with the greatest care, mixed cultures are at times unavoidable, a suitable nutrient agar plate may be streaked with the saline inoculum for overnight incubation and inspection to insure against inadvertently taking data based on a mixed culture.

During the period July-December of 1977, independent clinical evaluations of this invention took place at four laboratories under the coordination of the Antimicrobic Investigation Section, Bacteriology Division of the Center for Disease Control, Atlanta, Georgia. Participating in this four-center clinical study were, alphabetically: Dr. Thomas L. Gavan (Department of Microbiology, the Cleveland Clinic Foundation, Cleveland, Ohio), Dr. Fritz D. Schoenknecht (University Hospital, University of Washington, Seattle, Washington), Dr. Clyde Thornsberry (Bacteriology Division, Bureau of Laboratories, Center for Disease Control, Atlanta, Georgia), and Dr. John A. Washington II, (Department of Laboratory Medicine, Mayo Clinic and Mayo Foundation, Rochester, Minnesota).

The clinical study took place in two phases. In the first phase (Phase I), the accuracy of the MIC determination of this invention was assessed relative to a microtube version of the ICS broth dilution method (henceforth called the reference method). In the second phase (Phase II), measures of both intralaboratory and interlaboratory reproducibility were determined within each of the two MIC determination methods. To accomplish the objectives of these two phases of the clinical trial, all investigators received the same lots of reagents and their own calibrated instrumentation, and they followed the same study design. This protocol called for each investigator to conduct parallel MIC determinations by both the new and reference methods throughout both phases of the study. The regression analysis technique employed by this invention provides equations that convert the light scattering data, measured in the presence of only two antimicrobial concentrations, into MIC values. MIC values obtained by using this analysis procedure were compared with the reference method. This enabled an examination of the accuracy (Phase I) and reproducibility (Phase II) of the MIC values derived in accordance with this invention relative to the reference MIC values.

In Phase I a total of 9,360 MIC determinations on 1260 bacterial strains were performed using this invention by all four investigators. At the same time 9,360 MIC determinations on the same 1260 strains were conducted in parallel with the reference method by the investigators. The total MIC determinations involved 104 antibiotic/"species" pairs, and each investigator tested the same frequencies of each "species" (14 in total) with the same panels of antibiotics. All 315 bacterial strains used in this phase of the study by each investigator were independently selected by that investigator, and were either recent clinical isolates (ca. 90% of total strains tested) from his laboratory or were stock cultures (ca. 10% of total strains tested) from his laboratory.

As shown in FIG. 10, overall comparisons of the 9,360 MIC determinations conducted showed the MIC determined with this invention to have approximately 95% agreement with the reference MIC, within the ± one two-fold dilution error of the reference broth dilution method. In other words, the three dimensional surfaces schematically depicted in FIGS. 4a–4c are within ± one two-fold dilution of approximately 95% of all the data points representing MIC values obtained by the reference method (including end points where MIC is determined as being simply greater or less than a given value).

The overall results of the individual investigators have also shown very high agreement ranging from 95.2% (Schoenknecht, Thornsberry and Washington) to 95.5% (Gaven).

On average, the investigators' results showed that the ten antibiotics in the study exhibited agreement levels all of which were above 90% and ranged from 92.1% (methicillin) to 98.1% (chloramphenicol) when compared to the reference results (FIG. 10).

Approximately 80% of the 9,360 parallel MIC determinations had at least one MIC value (i.e., either using this invention or the reference method) that was not on-scale. The remaining ca. 20% of the determinations were such that the MIC value measured by both methods was on-scale. If one selects this ca. 20% sub-population of MIC determinations and calculates the percent agreement between methods on this population, the results show agreement in 90% to 96.5% of the cases. Only small decreases in the overall percent agreement as well as in the individual antibiotic results occurred relative to the analogous percentages of agreement when all strains (i.e., on-scale and off-scale) were used. Thus, the MIC determined by this invention not only has good agreement with the reference MIC for each antibiotic when challenging all the strains tested, but also when challenging just the subset of strains having MIC values on-scale by both methods.

Analysis of the Phase I data on the basis of both the four major organism groups (i.e., Staphylococci, Enterococci, Enterobacteriaceae, and Gram negative glucose non-fermenters) and the fourteen species categories has also been carried out for each antibiotic and investigator. Of the 27 antibiotic/major organism pairs tested by all investigators, 96.3% (26) had agreement levels of 85% when MIC determined in accordance with this invention was compared with the reference method. In only one case was the agreement less than 85% (penicillin G/Staphylococci, 83.8%). More specifically 92.3% (24) of the above 26 antibiotic/organism pairs tested had agreement levels of 90% or above and of these 24, 75% (18) had agreement levels of 95%. On the basis of individual species, the results obtained with this invention also exhibited very good agreement with the reference method averaged over all antibiotics used. More specifically, in terms of the individual antibiotic/"species" combinations of 104 antibiotic/"species" pairs tested, 95.2% (99) had agreement levels of at least 85% when compared with the reference method. Furthermore, 91.9% (91) of these 99 pairs had agreement levels of 90% and of these 91, 91.3% (74) had agreement levels of at least 95%.

It should also be noted that the strains selected by the individual investigators to fill their quotas of the various species were such as to adequately represent the known resistant subpopulation(s) to the various antibiotics. The accuracy in the comparison of the results obtained with this invention with the reference MIC values for each antibiotic is very good. In this regard, the generally symmetrical distribution of two-fold differences in the MIC's of these two methods (about the point of zero absolute MIC difference) is also excellent.

In the second phase (Phase II) of this clinical investigation each investigator received the same set of 56 strains (14 "species" categories×4 strains per category) from the coordinating laboratory. They were received by each laboratory as frozen blood samples and multiple copies of each of the 56 were received to enable intralaboratory replications. The previous MIC data of these strains was not known to any of the persons conducting the parallel Autobac/reference MIC testing at the four laboratories. Each participating laboratory tested in parallel each of the strains on three separate days, using the same panels of antibiotics as used in Phase I. In this manner, 3 intralaboratory replicate determinations of each of 4 strains per species category were collected by the parallel methods at each of the four laboratories. In this way the body of data for arriving at statistical measures of both intralaboratory and interlaboratory variability/reproducibility were collected.

Three different and complementary statistical analyses were conducted on the body of Phase II data. On the basis of these analyses certain reliable conclusions have emerged. One of these conclusions is that the ±1 SD variability (both intra- and interlaboratory) of this invention is significantly less than that for the reference method. Furthermore, in terms of intralaboratory considerations, the present invention, was found to have significantly less variability and equivalent reproducibility to the reference method. Similarly, in terms of interlaboratory considerations, the invention was found to have significantly less variability than, and equivalent reproducibility to, the reference method.

In view of the combined results of both Phases I and II it has been concluded that the method of this invention using fixed relationships determined by regression analysis, is accurate relative to the reference method for each antibiotic tested, and that this method has significantly less variability and comparable reproducibility to the reference method for these ten antibiotics.

While only one presently preferred exemplary embodiment of this invention has been described in detail, it will be appreciated that many modifications and variations may be made in that embodiment while still retaining many of its novel and advantageous features as set forth in the following claims.

What is claimed is:

1. A method for determining the minimum inhibitory concentration (MIC) of a given antimicrobic agent with respect to a sampled microorganism, said method comprising the steps of:
   (a) distributing a portion of said sampled microorganism to a bacteria growth medium in at least two separate chambers;
   (b) distributing a first concentration of said given antimicrobic agent to a first one of said chambers and a second different concentration of said given antimicrobic agent to a second one of said chambers;
   (c) detecting the amounts of microorganism growth occurring in said first and second chambers after a predetermined incubation interval by measuring the respective numerical concentrations of microorganisms residing in said chambers as compared to growth occurring in a control chamber having no antimicrobic agent therein and providing respectively corresponding first and second measured values of such growth; and
   (d) determining the minimum inhibitory concentration (MIC) of said given antimicrobic agent for said sampled microorganisms as a predetermined function of at least said first and second measured values of microorganism growths.

2. A method as in claim 1 including the step of establishing said predetermined function in advance thus facilitating the rapid determination of MIC whenever a suitable microorganism sample is presented, said step of establishing comprising:
   measuring the MIC for plural microorganisms of a given general class using accepted quantitative measurement techniques;
   also performing steps (a), (b) and (c) for each of said plural microorganisms used in said measuring step; and
   using the data resulting from the two just-above recited steps to establish said predetermined function for a given antimicrobic agent and a given general class of microorganisms.

3. A method as in claim 1 or 2 wherein said predetermined function is in the form of a table having discrete entries for predetermined increments of measured growth.

4. A method as in claim 1 or 2 wherein said predetermined function is in the form of an equation providing an MIC value for a given set of said first and second measured values of microorganism growth.

5. A method as in claim 1 or 2 wherein said general class of microorganisms is one of the general classes of bacteria: Staphylococci, Enterococci, Enterobacteriaceae, and gram-negative glucose non-fermenters.

6. A method as in claim 1 or 2 wherein said given antimicrobic agent is an antibiotic of the group comprising: Ampicillin, Carbenicillin, Cephalothin, Chloramphenicol, Clindamycin, Gentamicin, Kanamycin, Methicillin, Penicillin G, and Tetracycline.

7. A method as in claim 1 or 2 wherein said general class of microorganisms is one of the general classes of bacteria Staphylococci, Enterococci, Enterobacteriaceae, and gram-negative glucose non-fermenters and wherein said given antimicrobic agent is an antibiotic of the group comprising Ampicillin, Carbenicillin, Cephalothin, Chloramphenicol, Clindamycin, Gentamicin, Kanamycin, Methicillin, Penicillin G, and Tetracycline.

8. A method as in claim 1 or 2 wherein said predetermined incubation interval is substantially less than that which would result in only extreme saturated "growth" or "no growth" conditions for substantially all measured amounts of microorganism growth.

9. A method as in claim 1 or 2 wherein said predetermined incubation interval is substantially less than 16 hours.

10. A method as in claim 1 or 2 wherein said predetermined incubation interval is approximately five hours.

11. A method for determining the minimum concentration of a predetermined antimicrobic agent necessary to at least inhibit the activity of sampled pathogenic organisms taken from a predetermined general class of organisms, said method comprising the steps of:
   (a) obtaining plural samples from said predetermined general class of organisms;
   (b) measuring the growth of each of said plural samples occurring in a growth medium during a predetermined incubation time in the presence of a first predetermined concentration of said predetermined antimicrobic agent;

(c) measuring said minimum concentration by a standard quantitative technique for each of said plural samples;

(d) establishing a fixed functional relationship between said measured growths and said measured minimum concentrations resulting from steps (b) and (c) for said predetermined general class of organisms and said predetermined antimicrobic agent;

(e) distributing said sampled pathogenic organism to said growth medium and measuring the growth of the organism occurring during a predetermined incubation time in the presence of said first predetermined concentration of said predetermined antimicrobic agent under conditions substantially the same as those occurring during step (b); and (f) determining said minimum concentration for the sampled pathogenic organism in accordance with said fixed functional relationship using the measured growth detected during step (e).

12. A method as in claim 11 further comprising the steps of:

(g) measuring the growth of each of said plural samples occurring in said growth medium during a predetermined incubation time in the presence of a second predetermined concentration of said predetermined antimicrobic agent;

(h) deriving said fixed functional relationship in step (d) as a function of the measured growth for said second predetermined concentration in addition to that occurring for said first predetermined concentration;

(i) distributing said sampled pathogenic organism to said growth medium and measuring the growth of the organism occurring during a predetermined incubation time in the presence of said second predetermined concentration of said predetermined antimicrobic agent under conditions substantially the same as those occurring during step (g); and (j) determining said minimum concentration for the sampled pathogenic organism in step (f) in accordance with said fixed functional relationship using both the measured growth detected during step (e) and that detected during step (i).

13. A method as in claim 11 or 12 wherein said minimum concentration is the minimum inhibitory concentration (MIC).

14. A method as in claim 11 wherein steps (a), (b), (c) and (d) are performed in advance thus providing said fixed functional relationship for ready use in rapidly performing steps (e) and (f) to determine said minimum concentration upon presentation of said sampled pathogenic organism.

15. A method as in claim 12 wherein steps (a), (b), (c), (d), (g) and (h) are performed in advance thus providing said fixed functional relationship for ready use in rapidly performing steps (e), (f), (i) and (j) to determine said minimum concentration upon presentation of said sampled pathogenic organism.

16. A method as in any of claims 11, 12, 14 or 15 wherein said fixed functional relationship is in the form of a table having discrete entries for predetermined increments of measured growth.

17. A method as in any of claims 11, 12, 14 or 15 wherein said fixed functional relationship is in the form of an equation providing a minimum concentration value for the measured growth values corresponding to said sampled pathogenic organism.

18. A method as in claim 11 or 12 wherein said predetermined general classes of organisms comprise Staphylococci, Enterococci, Enterobacteriaceae, and gram-negative glucose non-fermenters.

19. A method as in claim 11 or 12 wherein said predetermined antimicrobic agent is an antibiotic of the group comprising: Ampicillin, Carbenicillin, Cephalothin, Chloramphenicol, Clindamycin, Gentamicin, Kanamycin, Methicillin, Penicillin G, and Tetracycline.

20. A method as in claim 11 or 12 wherein said general class of microorganisms is one of the general classes of bacteria Staphylococci, Enterococci, Enterobacteriacae, and gram-negative glucose non-fermenters and wherein said predetermined antimicrobic agent is an antibiotic of the group comprising Ampicillin, Carbenicillin, Cephalothin, Chloramphenicol, Clindamycin, Gentamicin, Kanamycin, Methicillin, Penicillin G, and Tetracycline.

21. A method as in claim 11 or 12 wherein said predetermined incubation interval is substantially less than that which would result in only extreme saturated "growth" or "no growth" conditions for substantially all measured amounts of microorganism growth.

22. A process which facilitates a relatively rapid and accurate quantitative determination of the minimum concentration of a predetermined antimicrobic agent necessary to at least inhibit the growth of a particular microorganism taken from a predetermined general class of microorganisms, said process comprising the steps of:

mixing a sample of said particular microorganisms into a liquid growth medium to provide a standardized concentration of microorganism colony forming units therein;

distributing said liquid growth medium with intermixed microorganism into plural separate chambers;

also separately introducing antimicrobic agent-containing materials into predetermined one of said chambers to provide respectively corresponding predetermined concentrations of antimicrobic agent therein;

incubating said chambers until said microorganisms have grown in number to a standardized concentration in a chamber where such growth is permitted to occur;

effectively measuring the number of microorganisms in said predetermined ones of said chambers still existing after such incubation period; and utilizing the measurements thus obtained to determine said minimum concentration using a predetermined fixed functional relationship which exists between such minimum concentration and the obtained measurements for a given combination of antimicrobic agent and the general class of microorganisms to which said sample corresponds.

23. A process as in claim 22 wherein only two of said measurements, respectively corresponding to two different antimicrobic agent concentrations, are utilized to determine said minimum concentration.

24. A process as in claim 22 wherein said predetermined concentrations of antimicrobic agent span the normally expected therapeutic range of concentrations for the antibiotic.

25. A process as in claim 22 wherein said predetermined fixed functional relationship has been previously determined by regression analysis using values of minimum concentrations determined by accepted standard quantitative analysis and values of microorganism growth observed under similar growth conditions for other microorganisms taken from the same general class as said sample.

26. A process as in any of claims 22-25 wherein said minimum concentration is the minimum inhibitory concentrations (MIC).

27. A process as in any of claims 22-25 wherein said predetermined fixed functional relationship is in the form of a table having discrete entries for predetermined increments of measured values.

28. A process as in any of claims 22-25 wherein said predetermined fixed functional relationship is in the form of an equation providing a calculable value for given measured values.

29. A process as in any of claims 22-25 wherein said predetermined general classes of microorganisms comprise Staphylococci, Enterococci, Enterobacteriaceae, and gram-negative glucose non-fermenters.

30. A process as in any of claims 22-25 wherein said predetermined antimicrobic agent is an antibiotic of the group comprising: Ampicillin, Carbenicillin, Cephalothin, Chloramphenicol, Clindamycin, Gentamicin, Kanamycin, Methicillin, Penicillin G, and Tetracycline.

31. A process as in any of claims 22-25 wherein said general class of microorganisms is one of the general classes of bacteria Staphylococci, Enterococci, Enterobacteriaceae, and gram-negative glucose non-fermenters and wherein said predetermined antimicrobic agent is an antibiotic of the group comprising Ampicillin, Carbenicillin, Cephalothin, Chloramphenicol Clindamycin, Gentamicin, Kanamycin, Methicillin, Penicillin G, and Tetracycline.

32. A method as in any of claims 22-25 wherein said standardized concentration existing after incubation is less than a saturated "growth" concentration.

33. A method as in any of claims 22-25 wherein said standardized concentration is at least three generations or doublings of growth as compared to the starting concentration of microorganisms.

34. Apparatus for determining the minimum concentration of a predetermined antimicrobic agent necessary to at least inhibit the activity of sampled pathogenic microorganisms taken for a predetermined general class of microorganisms, said apparatus comprising:
 a plurality of separate chambers, each adapted to contain said sampled pathogenic microorganism within a growth medium and a respectively correspondingly predetermined concentration of a predetermined antimicrobic agent;
 growth measurement means for measuring the amounts of microorganism growth occurring in each of said plural chambers after a predetermined incubation interval; and
 computation means adapted to determine and provide the value of said minimum concentration as a predetermined function of said measured amounts of growth for a given combination of antimicrobic agent and general class of microorganisms.

35. Apparatus as in claim 34 wherein said computation means comprises a table having discrete entries for predetermined increments of measured growth.

36. Apparatus as in claim 34 wherein said computation means comprises an equation providing a calculable minimum concentration for a given set of measured growths.

37. Apparatus for determining the minimum inhibitory concentration (MIC) of a given antimicrobic agent with respect to a sampled microorganism from a given general class comprising:
 means for measuring the amounts of growth of said sampled microorganisms during a predetermined time period in the presence of a predetermined number of respective predetermined concentrations of said antimicrobic agent and for providing electrical signals representative of such measured growth; and
 means responsive to said electrical signals for automatically determining a substantially exact value of said MIC from said measured amounts of growth, said determined value of said MIC not being limited to said predetermined concentrations.

* * * * *